US011542313B2

(12) United States Patent
Alsina-Fernandez et al.

(10) Patent No.: US 11,542,313 B2
(45) Date of Patent: Jan. 3, 2023

(54) INCRETIN ANALOGS AND USES THEREOF

(71) Applicant: Eli Lilly and Company, Indianapolis, IN (US)

(72) Inventors: Jorge Alsina-Fernandez, Indianapolis, IN (US); Tamer Coskun, Carmel, IN (US); Lili Guo, Carmel, IN (US); Hongchang Qu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 37 days.

(21) Appl. No.: 16/768,960

(22) PCT Filed: Dec. 14, 2018

(86) PCT No.: PCT/US2018/065663
§ 371 (c)(1),
(2) Date: Jun. 2, 2020

(87) PCT Pub. No.: WO2019/125938
PCT Pub. Date: Jun. 27, 2019

(65) Prior Publication Data
US 2020/0331980 A1    Oct. 22, 2020

Related U.S. Application Data

(60) Provisional application No. 62/608,613, filed on Dec. 21, 2017.

(51) Int. Cl.
*C07K 14/605*    (2006.01)
*A61K 38/00*    (2006.01)

(52) U.S. Cl.
CPC ............ *C07K 14/605* (2013.01); *A61K 38/00* (2013.01)

(58) Field of Classification Search
CPC ...... A61K 38/26; A61K 38/00; C07K 14/605; A61P 1/16; A61P 3/04; A61P 3/06; A61P 3/10
See application file for complete search history.

(56) References Cited

U.S. PATENT DOCUMENTS 9,474,780 B2 * 10/2016 Bokvist .................. A61K 45/06
2021/0221865 A1 * 7/2021 Alsina-Fernandez ........................ A61K 38/26

FOREIGN PATENT DOCUMENTS

WO    2010108937 A3    9/2010
WO    2015067715 A2    5/2015
WO    2015067716 A1    5/2015

OTHER PUBLICATIONS

Betts et al. Amino Acids Properties and Consequences of Substitutions. Chapter 14 in "Bioinformatics for Geneticists", 2003, pp. 289-316. (Year: 2003).*
Nørregaard, P. K., Deryabina, M. A., Tofteng Shelton, P., Fog, J. U., Daugaard, J. R., Eriksson, P. O., ... & Jessen, L. (2018). A novel GIP analogue, ZP 4165, enhances glucagon-like peptide-1-induced body weight loss and improves glycaemic control in rodents. *Diabetes, Obesity and Metabolism*, 20(1), 60-68.
Bachem, Peptides in Diabetes, Peptide Trends, Oct. 2017.
Coskun T, Sloop KW, Loghin C, Alsina-Fernandez J, Urva S, Bokvist KB, Cui X, Briere DA, Cabrera O, Roell WC, et al. 2018 LY3298176, a novel dual GIP and GLP-1 receptor agonist for the treatment of type 2 diabetes mellitus: From discovery to clinical proof of concept. Mol Metab 18 3-14.
Frias, J. P., Nauck, M. A., Van, J., Kutner, M. E., Cui, X., Benson, C., ... & Haupt, A. (2018). Efficacy and safety of LY3298176, a novel dual GIP and GLP-1 receptor agonist, in patients with type 2 diabetes: a randomised, placebo-controlled and active comparator-controlled phase 2 trial. *The Lancet*, 392(10160), 2180-2193.
International Searching Authority, International Search Report for PCT/US2018/065605, dated Mar. 27, 2019.
International Searching Authority, Written Opinion for PCT/US2018/065605, dated Mar. 27, 2019.
Jensen, L., Helleberg, H., Roffel, A., van Lier, J. J., Bjørnsdottir, I., Pedersen, P. J., ... & Pedersen, M. L. (2017). Absorption, metabolism and excretion of the GLP-1 analogue semaglutide in humans and nonclinical species. *European Journal of Pharmaceutical Sciences*, 104, 31-41.

* cited by examiner

*Primary Examiner* — Marcela M Cordero Garcia
(74) *Attorney, Agent, or Firm* — Rita Sanzgiri

(57) ABSTRACT

Incretin analogs are provided that have activity at each of the GIP, GLP-1 and glucagon receptors. The incretin analogs have structural features resulting in balanced activity and extended duration of action at each of these receptors. Methods also are provided for treating diseases such as diabetes mellitus, dyslipidemia, fatty liver disease, metabolic syndrome, non-alcoholic steatohepatitis and obesity.

26 Claims, No Drawings
Specification includes a Sequence Listing.

INCRETIN ANALOGS AND USES THEREOF

REFERENCE TO SEQUENCE LISTING

The instant application contains a Sequence Listing submitted electronically as an ASCII plain text file, named X21606 8 Nov. 2022 Updated Sequence Listing_ST25.txt, created on 8 Nov. 2022 and 25 KB in size. The Sequence Listing information is incorporated herein by reference in its entirety.

This disclosure relates to incretin analogs having activity at each of a glucose-dependent insulinotropic polypeptide (GIP), glucagon-like peptide-1 (GLP-1) and glucagon receptors. The incretin analogs described herein have structural features that provide balanced activity and have extended duration of action at each of these receptors. Such incretin analogs may be useful for treating disorders such as type 2 diabetes mellitus (T2DM), dyslipidemia, metabolic syndrome, non-alcoholic fatty liver disease (NAFLD), non-alcoholic steatohepatitis (NASH) and/or obesity.

Over the past several decades, the prevalence of diabetes has continued to rise. T2DM is the most common form of diabetes accounting for about 90% of all diabetes. T2DM is characterized by high blood glucose levels caused by insulin resistance. The current standard of care for T2DM includes diet and exercise, as well as treatment with oral medications and injectable glucose-lowering drugs including incretin-based therapies, such as GLP-1 receptor agonists.

GLP-1 is a 36-amino acid peptide, the major biologically active fragment of which is produced as a 30-amino acid, C-terminal amidated peptide (GLP-$1_{7-36}$; SEQ ID NO:2) that stimulates glucose-dependent insulin secretion and that prevents hyperglycemia in diabetics. A variety of GLP-1 analogs are currently available for treating T2DM, including dulaglutide, exenatide and liraglutide. Many currently marketed GLP-1 receptor agonists, however, are dose-limited by gastrointestinal side effects, such as nausea and vomiting. When treatment with oral medications and incretin-based therapies is insufficient, insulin is considered. Despite the treatment options available, significant numbers of individuals receiving approved therapies are not reaching glycemic control goals (see, e.g., Casagrande et al. (2013) *Diabetes Care* 36:2271-2279).

Uncontrolled diabetes can lead to one or more conditions that impact morbidity and mortality of such individuals. One of the main risk factors for T2DM is obesity, and a majority of individuals with T2DM (~90%) are overweight or obese. It is documented that a decrease in body adiposity will lead to improvement in obesity-associated co-morbidities including hyperglycemia and cardiovascular events. Therefore, therapies effective in glucose control and weight reduction are needed for better disease management.

In view thereof, new therapies being studied include compounds having not only activity at a GLP-1 receptor but also activity at one or more other receptors, such as the GIP and/or glucagon receptors. In fact, certain compounds have been described as having triple agonist activity (i.e., activity at each of the GIP, GLP-1 and glucagon receptors). For example, Int'l Patent Application Publication No. WO 2015/067716 describes glucagon analogs having triple agonist activity. Similarly, Int'l Patent Application No. WO 2016/198624 describes analogs of exendin-4, itself a GLP-1 analog, having triple agonist activity. Likewise, Int'l Patent Application Nos. WO 2014/049610 and WO 2017/116204 each describe a variety of analogs having triple agonist activity. Moreover, Int'l Patent Application No. WO 2017/153375 describes glucagon and GLP-1 co-agonists that also are stated to have GIP activity.

Nevertheless, a need remains for treatments, especially for T2DM, that are capable of providing effective glucose control, with weight loss benefits and a favorable side effect profile. There also is a need for therapeutic agents available for use with sufficiently extended duration of action to allow for dosing as infrequently as once a day, thrice-weekly, twice-weekly or once a week.

The incretin analogs described herein seek to meet the needs above. Accordingly, this disclosure describes incretin analogs with activity at each of the GIP, GLP-1 and glucagon receptors. Advantageously, the incretin analogs described herein have balanced activity allowing for administration of doses that provide sufficient activity at each receptor to provide the benefits of agonism of that receptor while avoiding unwanted side effects associated with too much activity. Moreover, the incretin analogs described herein have extended duration of action at each of the GIP, GLP-1 and glucagon receptors allowing for dosing as infrequently as once-a-day, thrice-weekly, twice-weekly or once-a-week. In this manner, the incretin analogs result in enhanced glucose control, metabolic benefits such as body weight lowering and/or improved body composition, lipid benefits such as proprotein convertase subtilisin/kexin type 9 (PCSK9) lowering, and/or other benefits such as an increase in bone mass or bone formation or a decrease in bone resorption. This disclosure also describes effective treatments for other disorders or conditions, including obesity, NAFLD, NASH, dyslipidemia, and/or metabolic disorder.

In one embodiment, an incretin analog is provided that includes the formula:

YX$_2$QGTFTSDYSIX$_{13}$LDKX$_{17}$AX$_{19}$X$_{20}$AFIEYLLX$_{28}$X$_{29}$GPSSX$_{34}$APPP S, where X$_2$ is Aib, X$_{13}$ is L or αMeL, X$_{17}$ is any amino acid with a functional group available for conjugation, and the functional group is conjugated to a C$_{16}$-C$_{22}$ fatty acid, X$_{19}$ is Q or A, X$_{20}$ is Aib, αMeK, Q or H, X$_{28}$ is E or A, X$_{29}$ is G or Aib, X$_{34}$ is G or Aib (SEQ ID NO:5), and the C-terminal amino acid is optionally amidated, or a pharmaceutically acceptable salt thereof.

In another embodiment, a method is provided for treating a disease such as dyslipidemia, fatty liver disease, metabolic syndrome, NASH, obesity and T2DM. Such methods can include at least a step of administering to an individual in need thereof an effective amount of an incretin analog described herein. In some instances, the disease is fatty liver disease, obesity, NASH or T2DM.

In another embodiment, an incretin analog as described herein is provided for use in therapy. For example, an incretin analog as described herein is provided for use in treating a disease such as dyslipidemia, fatty liver disease, metabolic syndrome, NASH, obesity and T2DM. In some instances, the disease is fatty liver disease, obesity, NASH or T2DM.

In another embodiment, an incretin analog as described herein is provided for use in manufacturing a medicament for treating dyslipidemia, fatty liver disease, metabolic syndrome, NASH, obesity and T2DM. In some instances, the disease is fatty liver disease, obesity, NASH or T2DM.

In another embodiment, a pharmaceutical composition is provided that includes an incretin analog as described herein and a pharmaceutically acceptable carrier, diluent or excipient.

Unless defined otherwise, all technical and scientific terms used herein have the same meaning as commonly understood by one of skill in the art to which the disclosure pertains. Although any methods and materials similar to or equivalent to those described herein can be used in the practice or testing of the incretin analogs, pharmaceutical compositions, and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

GIP is a 42-amino acid peptide (SEQ ID NO:4) and is an incretin, which plays a physiological role in glucose homeostasis by stimulating insulin secretion from pancreatic beta cells in the presence of glucose.

GLP-1 is a 36-amino acid peptide (SEQ ID NO:2) and also is an incretin, which stimulates glucose-dependent insulin secretion and which has been shown to prevent hyperglycemia in diabetics.

Glucagon is a 29-amino acid peptide (SEQ ID NO:1) that helps maintain blood glucose by binding to and activating glucagon receptors on hepatocytes, causing the liver to release glucose—stored in the form of glycogen—through a process called glycogenolysis.

Oxyntomodulin (OXM) is a 37-amino acid peptide including not only the 29-amino acid sequence of glucagon but also an octapeptide carboxy terminal extension (SEQ ID NO:3) that activates both the glucagon and GLP-1 receptors, with a slightly higher potency for the glucagon receptor over the GLP-1 receptor.

In addition to T2DM, incretins and analogs thereof having activity at one or more of the GIP, GLP-1 and/or glucagon receptors have been described as having a potential for therapeutic value in a number of other conditions, diseases or disorders, including, for example, obesity, NAFLD and NASH, dyslipidemia, metabolic syndrome, bone-related disorders, Alzheimer's disease and Parkinson's disease. See, e.g., Jall et al. (2017) *Mol. Metab.* 6:440-446; Carbone et al. (2016) *J. Gastroenterol. Hepatol.* 31:23-31; Finan et al. (2016) *Trends Mol. Med.* 22:359-376; Choi et al. (2017) *Potent body weight loss and efficacy in a NASH animal model by a novel long-acting GLP-1/Glucagon/GIP triple-agonist (HM15211)*, ADA Poster 1139-P; Ding (2008) *J. Bone Miner. Res.* 23:536-543; Tai et al. (2018) *Brain Res.* 1678:64-74; Müller et al. (2017) *Physiol. Rev.* 97:721-766; Finan et al. (2013) *Sci. Transl. Med.* 5:209; Hölscher (2014) *Biochem. Soc. Trans.* 42:593-600.

As used herein, "about" means within a statistically meaningful range of a value or values such as, for example, a stated concentration, length, molecular weight, pH, sequence identity, time frame, temperature or volume. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of the GIP, GLP-1 or glucagon receptors, "activity," "activate," "activating" and the like means a capacity of a compound, such as the incretin analogs described herein, to bind to and induce a response at the receptor(s), as measured using assays known in the art, such as the in vitro assays described below.

As used herein, "amino acid with a functional group available for conjugation" means any natural or unnatural amino acid with a functional group that may be conjugated to fatty acid by way of, for example, a linker. Examples of such functional groups include, but are not limited to, alkynyl, alkenyl, amino, azido, bromo, carboxyl, chloro, iodo, and thiol groups. Examples of natural amino acids including such functional groups include K (amino), C (thiol), E (carboxyl) and D (carboxyl).

As used herein, "$C_{16}$-$C_{22}$ fatty acid" means a carboxylic acid having between 16 and 22 carbon atoms. The $C_{16}$-$C_{22}$ fatty acid suitable for use herein can be a saturated monoacid or a saturated diacid. As used herein, "saturated" means the fatty acid contains no carbon-carbon double or triple bonds.

As used herein, "effective amount" means an amount, concentration or dose of one or more incretin analogs described herein, or a pharmaceutically acceptable salt thereof which, upon single or multiple dose administration to an individual in need thereof, provides a desired effect in such an individual under diagnosis or treatment. An effective amount can be readily determined by one of skill in the art through the use of known techniques and by observing results obtained under analogous circumstances. In determining the effective amount for an individual, a number of factors are considered including, but not limited to, the species of mammal; its size, age and general health; the specific disease or disorder involved; the degree of or involvement of or the severity of the disease or disorder; the response of the individual patient; the particular incretin analog administered; the mode of administration; the bioavailability characteristics of the preparation administered; the dose regimen selected; the use of concomitant medication; and other relevant circumstances.

As used herein, "extended duration of action" means that binding affinity and activity for an incretin analog continues for a period of time greater than native human GIP, GLP-1 and glucagon peptides, allowing for dosing at least as infrequently as once daily or even thrice-weekly, twice-weekly or once-weekly. The time action profile of the incretin analog may be measured using known pharmacokinetic test methods such as those utilized in the examples below.

As used herein, "incretin analog" means a compound having structural similarities with, but multiple differences from, each of GIP, GLP-1 and glucagon, especially human GIP (SEQ ID NO:4), GLP-1 (SEQ ID NO:2) and glucagon (SEQ ID NO:1). The incretin analogs described herein include amino acid sequences resulting in the compounds having affinity for and activity at each of the GIP, GLP-1 and glucagon receptors (i.e., triple agonist activity).

As used herein, "individual in need thereof" means a mammal, such as a human, with a condition, disease, disorder or symptom requiring treatment or therapy, including for example, those listed herein.

As used herein, "treat," "treating," "to treat" and the like mean restraining, slowing, stopping or reversing the progression or severity of an existing condition, disease, disorder or symptom.

As used herein, and with reference to an incretin analog, "triple agonist activity" means an incretin analog with activity at each of the GIP, GLP-1 and glucagon receptors, especially an analog having a balanced and sufficient activity at each receptor to provide the benefits of agonism of that receptor while avoiding unwanted side effects associated with too much activity. Moreover, the incretin analogs having triple agonist activity have extended duration of action at each of the GIP, GLP-1 and glucagon receptors, which advantageously allows for dosing as infrequently as once-a-day, thrice-weekly, twice-weekly or once-a-week.

The structural features of the incretin analogs described herein result in analogs having sufficient activity at each of the GIP, GLP-1 and glucagon receptors to obtain the favorable effects of activity at each receptor (i.e., triple agonist activity), but not so much activity at any one receptor to either overwhelm the activity at the other two receptors or result in undesirable side effects when administered at a dose sufficient to result in activity at all three receptors. Non-limiting examples of such structural features in certain embodiments, and with reference to SEQ ID NO:5, include L or αMeL at position 13, which was found to contribute to optimal glucagon and GIP activity; Aib at position 20, which was found to contribute to optimal GIP activity; acylation at position 17, which was found to contribute to optimal glucagon activity; and Y at position 25, which was found to contribute to optimal glucagon and/or GIP activity. Other examples of such structural features include the amino acids described herein at positions 22, 24 and 28-39, which were found to contribute to optimal binding and potency at all three receptors.

The structural features of the incretin analogs described herein also result in analogs having many other beneficial attributes relevant to their developability as therapeutic treatments, including for improving solubility of the analogs in aqueous solutions, improving chemical and physical formulation stability, extending the pharmacokinetic profile, and minimizing potential for immunogenicity. Non-limiting examples of particular structural features that result in such attributes include acylation at position 17 with a $C_{20}$ fatty acid, which contributes to optimal pharmacokinetic (PK) profiles and developability; Aib, αMeK, Q or H at position 20, which contribute to optimal PK profiles and developability; and the amino acids positions 22, 24 and 28-39, which contribute to optimal PK, immunogenicity, developability and stability.

It should be noted that the foregoing lists of structural features are exemplary, and not comprehensive, and that the combination of beneficial characteristics of exemplary analogs described herein is not the result of any modification in isolation, but is instead achieved through the novel combinations of the structural features described herein. In addition, the above-described effects of the foregoing lists of modifications are not exclusive, as many of these modifications also have other effects important to the characteristics of the compounds described herein, as described below.

The amino acid sequences of incretin analogs described herein incorporate naturally occurring amino acids, typically depicted herein using standard one letter codes (e.g., L=leucine), as well as alpha-methyl substituted residues of natural amino acids (e.g., α-methyl leucine (αMeL) and α-methyl lysine (αMeK)), and certain other unnatural amino acids, such as alpha amino isobutyric acid (Aib). The structures of these amino acids are depicted below:

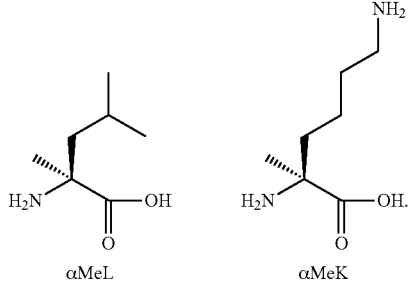

-continued

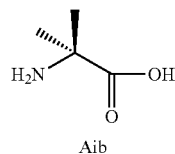

As noted above, the incretin analogs described herein have structural similarities to, but many structural differences, from any of the native human peptides. For example, when compared to native human GIP (SEQ ID NO:4), the incretin analogs described herein include modifications at one or more of positions 2, 3, 7, 13, 14, 17, 18-21, 23-25, 28-29 and 30-42. In some instances, the incretin analogs described herein include modifications to the amino acids of native human GIP (SEQ ID NO:4) at each of positions 2, 3, 7, 13, 14, 17, 18, 20, 21, 23-25, 29 and 30-42. In certain instances, the incretin analogs described herein include the following amino acid modifications: Aib at position 2; Q at position 3; T at position 7; L or αMeL at position 13; L at position 14; a modified K residue at position 17 that is modified through conjugation to the epsilon-amino group of the K-side chain with a $C_{16}$ to $C_{22}$ fatty acid, optionally through the use of a linker; A at position 18; A at position 21; I at position 23; E at position 24; Y at position 25; G or Aib at position 29; and replacement of the amino acids at positions 30-42 with an amino acid sequence selected from GPSSGAPPPS (SEQ ID NO:26) and GPSS-Aib-APPPS (SEQ ID NO:27) (and truncated analogs of the tail). In yet other instances, the incretin analogs described herein also include modifications at one or more of A at position 19; αMeK, Aib or H at position 20; and E at position 28. In certain instances, the incretin analogs described herein are amidated. In addition to the changes described herein, the incretin analogs described herein may include one or more additional amino acid modifications, provided, however, that the analogs remain capable of binding to and activating each of the GIP, GLP-1 and glucagon receptors.

As noted above, the incretin analogs described herein include a fatty acid moiety conjugated, for example, by way of a linker to a natural or unnatural amino acid with a functional group available for conjugation. Such a conjugation is sometimes referred to as acylation. In certain instances, the amino acid with a functional group available for conjugation can be K, C, E and D. In particular instances, the amino acid with a functional group available for conjugation is K, where the conjugation is to an epsilon-amino group of a K side-chain.

The acylation of the incretin analogs described herein is at position 17 in SEQ ID NO:5, which was determined to be the optimal location for inclusion of this structure. The fatty acid, and in certain embodiments the linker, act as albumin binders, and provide a potential to generate long-acting compounds.

The incretin analogs described herein utilize a $C_{16}$-$C_{22}$ fatty acid chemically conjugated to the functional group of an amino acid either by a direct bond or by a linker. The length and composition of the fatty acid impacts half-life of the incretin analogs, their potency in in vivo animal models, and their solubility and stability. Conjugation to a $C_{16}$-$C_{22}$ saturated fatty monoacid or diacid results in incretin analogs that exhibit desirable half-life, desirable potency in in vivo animal models, and desirable solubility and stability characteristics.

Examples of saturated $C_{16}$-$C_{22}$ fatty acids for use herein include, but are not limited to, palmitic acid (hexadecanoic acid) ($C_{16}$ monoacid), hexadecanedioic acid ($C_{16}$ diacid), margaric acid (heptadecanoic acid)($C_{17}$ monoacid), heptadecanedioic acid ($C_{17}$ diacid), stearic acid ($C_{18}$ monoacid), octadecanedioic acid ($C_{18}$ diacid), nonadecylic acid (nonadecanoic acid)($C_{19}$ monoacid), nonadecanedioic acid ($C_{19}$ diacid), arachadic acid (eicosanoic acid)($C_{20}$ monoacid), eicosanedioic acid ($C_{20}$ diacid), heneicosylic acid (heneicosanoic acid)($C_{21}$ monoacid), heneicosanedioic acid ($C_{21}$ diacid), behenic acid (docosanoic acid)($C_{22}$ monoacid), docosanedioic acid ($C_{22}$ diacid), including branched and substituted derivatives thereof.

In certain instances, the $C_{16}$-$C_{22}$ fatty acid can be a saturated $C_{18}$ monoacid, a saturated $C_{18}$ diacid, a saturated $C_{19}$ monoacid, a saturated $C_{19}$ diacid, a saturated $C_{20}$ monoacid, a saturated $C_{20}$ diacid, and branched and substituted derivatives thereof. In more particular instances, the $C_{16}$-$C_{22}$ fatty acid can be stearic acid, arachadic acid and eicosanedioic acid, especially arachadic acid.

In some instances, the linker can have from one to four amino acids, an amino polyethylene glycol carboxylate, or mixtures thereof. In certain instances, the amino polyethylene glycol carboxylate has the following structure:

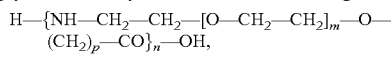

H—{NH—CH$_2$—CH$_2$—[O—CH$_2$—CH$_2$]$_m$—O—(CH$_2$)$_p$—CO}$_n$—OH, where m is any integer from 1 to 12, n is any integer from 1 to 12, and p is 1 or 2.

In certain instances, the linker can have one or more (2-[2-(2-amino-ethoxy)-ethoxy]-acetyl) moieties, optionally in combination with one to four amino acids.

In instances in which the linker includes at least one amino acid, the amino acid can be one to four Glu or γGlu amino acid residues. In some instances, the linker can include one or two Glu or γGlu amino acid residues, including the D-forms thereof. For example, the linker can include either one or two γGlu amino acid residues. Alternatively, the linker can include one to four amino acid residues (such as, for example, Glu or γGlu amino acids) used in combination with up to thirty-six (2-[2-(2-amino-ethoxy)-ethoxy]-acetyl) moieties. Specifically, the linker can be combinations of one to four Glu or γGlu amino acids and one to four (2-[2-(2-amino-ethoxy)-ethoxy]-acetyl) moieties. In other instances, the linker can be combinations of one or two γGlu amino acids and one or two (2-[2-(2-amino-ethoxy)-ethoxy]-acetyl) moieties.

In a specific instance, the incretin analogs described herein have linker and fatty acid components having the structure of the following formula:

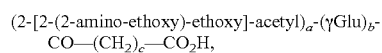

(2-[2-(2-amino-ethoxy)-ethoxy]-acetyl)$_a$-(γGlu)$_b$-CO—(CH$_2$)$_c$—CO$_2$H, where a is 0, 1 or 2, b is 1 or 2, and c is 16 or 18. In a particular instance, a is 2, b is 1, and c is 18, the structure of which is depicted below:

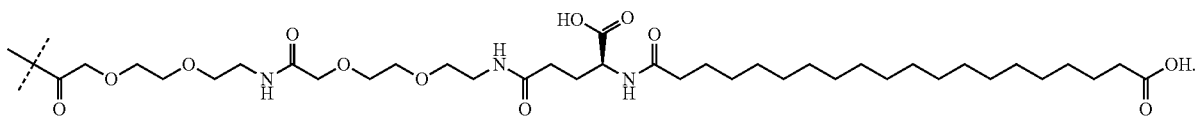

In another specific instance, a is 1, b is 2, and c is 18, the structure of which is depicted below:

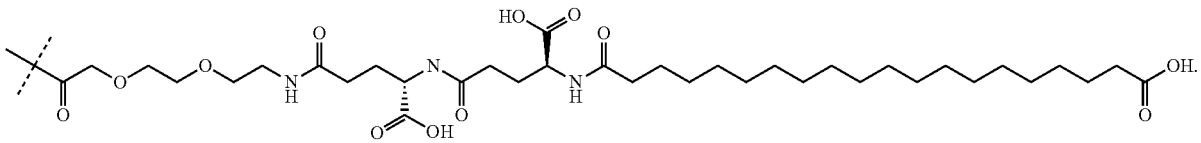

In another specific instance, a is 0, b is 2, and c is 18, the structure of which is depicted below:

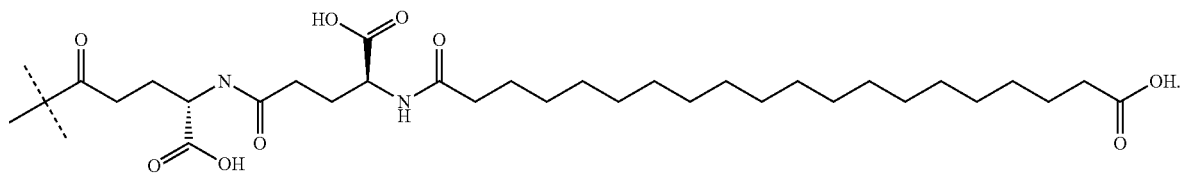

In another specific instance, a is 1, b is 1, and c is 18, the structure of which is depicted below:

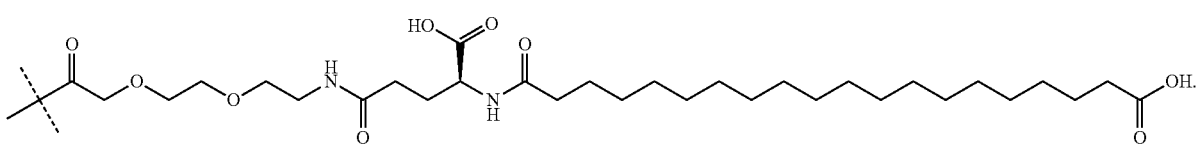

As shown in the chemical structures of Examples 1-20 below, the linker-fatty acid moieties described above can be linked to the epsilon (ε)-amino group of the lysine (K) side-chain.

The affinity of the incretin analogs described herein for each of the GIP, GLP-1 and glucagon receptors may be measured using techniques known in the art for measuring receptor binding levels, including, for example, those described in the examples below, and is commonly expressed as an inhibitory constant (Ki) value. The activity of the incretin analogs described herein at each of the receptors also may be measured using techniques known in the art, including, for example, the in vitro activity assays described below, and is commonly expressed as an effective concentration 50 ($EC_{50}$) value, which is the concentration of compound causing half-maximal simulation in a dose response curve.

The incretin analogs described herein can be formulated as pharmaceutical compositions, which can be administered by parenteral routes (e.g., subcutaneous, intravenous, intraperitoneal, intramuscular or transdermal). Such pharmaceutical compositions and techniques for preparing the same are well known in the art. See, e.g., Remington: The Science and Practice of Pharmacy (Troy, Ed., 21$^{st}$ Edition, Lippincott, Williams & Wilkins, 2006). In particular instances, the incretin analogs are administered subcutaneously.

The incretin analogs described herein may react with any of a number of inorganic and organic acids/bases to form pharmaceutically acceptable acid/base addition salts. Pharmaceutically acceptable salts and common techniques for preparing them are well known in the art (see, e.g., Stahl et al., Handbook of Pharmaceutical Salts: Properties, Selection and Use, 2$^{nd}$ Revised Edition (Wiley-VCH, 2011)). Pharmaceutically acceptable salts for use herein include sodium, trifluoroacetate, hydrochloride and/or acetate salts.

The disclosure also provides and therefore encompasses novel intermediates and methods of synthesizing the incretin analogs described herein, or a pharmaceutically acceptable salts thereof. The intermediates and incretin analogs described herein can be prepared by a variety of techniques known in the art. For example, a method using chemical synthesis is illustrated in the Examples below. The specific synthetic steps for each of the routes described may be combined in different ways to prepare the incretin analogs described herein. The reagents and starting materials are readily available to one of skill in the art.

Certain incretin analogs described herein are generally effective over a wide dosage range. For example, dosages for once-weekly administration may fall within a range of about 0.01 to about 30 mg/person/week, within a range of about 0.1 to about 10 mg/person/week or even within a range of about 0.1 to about 3 mg/person/week. Thus, the incretin analogs described herein may be dosed daily, thrice-weekly, twice-weekly or once-weekly, especially once-weekly administration.

The incretin analogs described herein may be used for treating a variety of conditions, disorders, diseases or symptoms. In particular, methods are provided for treating T2DM in an individual, where such methods include at least a step of administering to an individual in need of such treatment an effective amount of an incretin analog described herein, or a pharmaceutically acceptable salt thereof.

Additionally, methods are provided for treating obesity in an individual, where such methods include at least a step of administering to an individual in need of such treatment an effective amount of an incretin analog described herein, or a pharmaceutically acceptable salt thereof.

Additionally, methods are provided for inducing non-therapeutic weight loss in an individual, where such methods include at least a step of administering to an individual in need of such treatment an effective amount of an incretin analog described herein, or a pharmaceutically acceptable salt thereof.

Additionally, methods are provided for treating metabolic syndrome in an individual, where such methods include at least a step of administering to an individual in need of such treatment an effective amount of an incretin analog described herein, or a pharmaceutically acceptable salt thereof.

Additionally, methods are provided for treating NASH in an individual, where such methods include at least a step of administering to an individual in need of such treatment an effective amount of an incretin analog described herein, or a pharmaceutically acceptable salt thereof.

Additionally, methods are provided for treating NAFLD in an individual, where such methods include at least a step of administering to an individual in need of such treatment an effective amount of an incretin analog described herein, or a pharmaceutically acceptable salt thereof.

In these methods, effectiveness of the incretin analogs can be assessed by, for example, observing a significant reduction in blood glucose, observing a significant increase in insulin, observing a significant reduction in HbA1c and/or observing a significant reduction in body weight.

Alternatively, the incretin analogs described herein or pharmaceutically acceptable salts thereof may be used for improving bone strength in an individual in need thereof. In some instances, the individual in need thereof has hypo-ostosis or hypo-osteoidosis, or is healing from bone fracture, orthotic procedure, prosthetics implant, dental implant, and/or spinal fusion. The incretin analogs described herein also may be used for treating other disorders such as Parkinson's disease or Alzheimer's disease.

Peptide Synthesis

EXAMPLE 1

Example 1 is a compound represented by the following description:

```
                                              (SEQ ID NO: 7)
Y-Aib-QGTFTSDYSI-αMeL-LDKK((2-[2-(2-2-aminoethoxy)-ethoxy]-acetyl)2-(γGlu)-CO—(CH2)18—CO2H)AQ- αMeK-AFIEYLLA-Aib-GPSSGAPPPS-NH2.
```

Below is a depiction of the structure of Example 1 (SEQ ID NO:7) using the standard single letter amino acid codes with the exception of residues Aib2, αMeL13, K17, αMeK20 and Aib29, where the structures of these amino acid residues have been expanded:

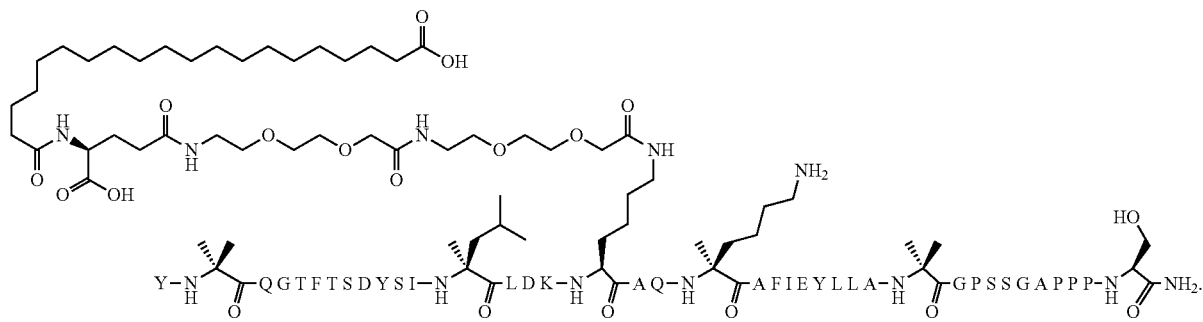

The peptide backbone of Example 1 is synthesized using Fluorenyimethyloxycarbonyl (Fmoc)/tert-Butyl (t-Bu) chemistry on a Symphony 12-Channel Multiplex Peptide Synthesizer (Protein Technologies, Inc. Tucson, Ariz.).

The resin consists of 1% DVB cross-linked polystyrene (Fmoc-Rink-MBHA Low Loading Resin, 100-200 mesh, EMD Millipore) at a substitution of 0.3-0.4 meq/g. Standard side-chain protecting groups are used. Fmoc-Lys(Mtt)-OH is used for the lysine at position 17, and Boc-Tyr(tBu)-OH is used for the tyrosine at position 1. Fmoc groups are removed prior to each coupling step (2×7 minutes) using 20% piperidine in DMF. All standard amino acid couplings are performed for 1 hour to a primary amine and 3 hour to a secondary amine, using an equal molar ratio of Fmoc amino acid (0.3M), diisopropylcarbodiimide (0.9M) and Oxyma (0.9M), at a 9-fold molar excess over the theoretical peptide loading. Exceptions are couplings to Cα-methylated amino acids, which are coupled for 3 hours. After completion of the synthesis of the peptide backbone, the resin is thoroughly washed with DCM for 6 times to remove residual DMF. The Mtt protecting group on the lysine at position 17 is selectively removed from the peptide resin using two treatments of 30% hexafluoroisopropanol (Oakwood Chemicals) in DCM (2×40-minute treatment).

Subsequent attachment of the fatty acid-linker moiety is accomplished by coupling of 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-Glu-OtBu, Ark Pharm, Inc.), mono-OtBu-eicosanedioic acid (WuXi AppTec, Shanghai, China). 3-fold excess of reagents (AA: PyAOP:DIPEA=1:1:1 mol/mol) are used for each coupling that is 1-hour long.

After the synthesis is complete, the peptide resin is washed with DCM, and then thoroughly air-dried. The dry resin is treated with 10 mL of cleavage cocktail (trifluoroacetic acid:water:triisopropylsilane, 95:2.5:2.5 v/v) for 2 hours at room temperature. The resin is filtered off, washed twice each with 2 mL of neat TFA, and the combined filtrates are treated with 5-fold cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times and dried in vacuo. The crude peptide is solubilized in 20% acetonitrile/20% acetic acid/60% water and purified by RP-HPLC on a Luna 5 μm Phenyl-Hexyl Preparative Column (21×250 mm, Phenomenex) with linear gradients of 100% acetonitrile and 0.1% TFA/water buffer system (30-50% acetonitrile in 60 min). The purity of peptide is assessed using analytical RP-HPLC and pooling criteria is >95%. The main pool purity of Example 1 is found to be 98.8%. Subsequent lyophilization of the final main product pool yields the lyophilized peptide TFA salt. The molecular weight is determined by LC-MS (obsd: M+4H+/4=1226.8; Calc M+4H+/4=1226.9).

EXAMPLE 2

Example 2 is a compound represented by the following description:

```
                                            (SEQ ID NO: 6)
Y-Aib-QGTFTSDYSI-αMeL-LDKK((2-[2-(2-aminoethoxy)-ethoxy]-acetyl)-(γGlu)-CO-(CH2)18-CO2H)

AQHAFIEYLLA-Aib-GPSSGAPPPS-NH2.
```

Below is a depiction of the structure of Example 2 (SEQ ID NO:6) using the standard single letter amino acid codes with the exception of residues Aib2, αMeL13, K17 and Aib29, where the structures of these amino acid residues have been expanded:

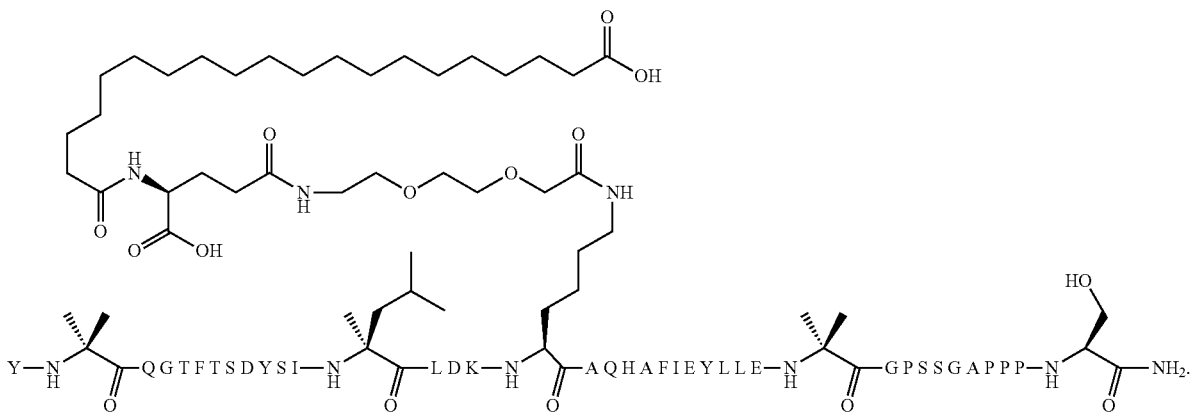

Similar processes to those described above for Example 1 are used to synthesize the peptide backbone, to conjugate the fatty acid-linker moiety, to examine the purity, and to confirm the molecular weight of Example 2.

EXAMPLE 3

Example 3 is a compound represented by the following description:

(SEQ ID NO: 8)
Y-Aib-QGTFTSDYSI-αMeL-LDKK((2-[2-(2-amino-ethoxy)-ethoxy]-acetyl)$_2$-(γGlu)-CO—(CH$_2$)$_{18}$—CO$_2$H)AQ-αMeK-AFIEYLLEGGPSSGAPPPS-NH$_2$.

Below is a depiction of the structure of Example 3 (SEQ ID NO:8) using the standard single letter amino acid codes with the exception of residues Aib2, αMeL13, K17, and αMeK20, where the structures of these amino acid residues have been expanded:

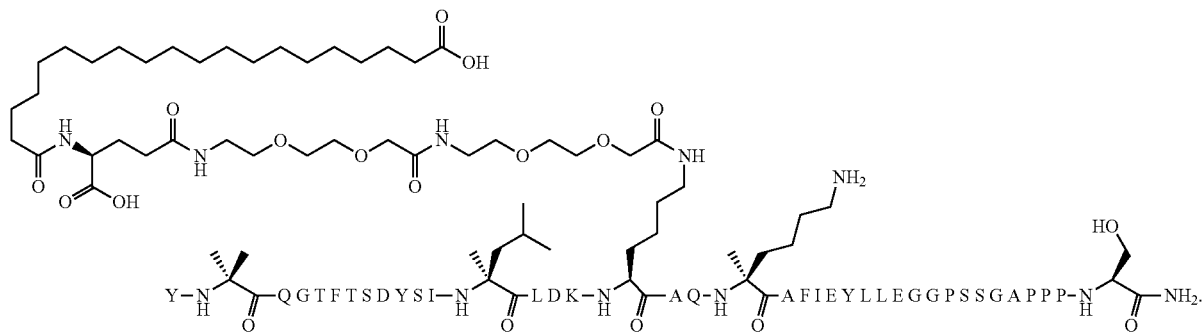

Similar processes to those described above for Example 1 are used to synthesize the peptide backbone, to conjugate the fatty acid-linker moiety, to examine the purity, and to confirm the molecular weight of Example 3.

EXAMPLE 4

Example 4 is a compound represented by the following description:

(SEQ ID NO: 9)
Y-Aib-QGTFTSDYSILLDKK((2-[2-(2-amino-ethoxy)-ethoxy]-acetyl)-(γGlu)-CO—(CH$_2$)$_{18}$—CO$_2$H)AQ-Aib-AFIEYLLA-Aib-GPSSGAPPPS-NH$_2$.

Below is a depiction of the structure of Example 4 (SEQ ID NO:9) using the standard single letter amino acid codes with the exception of residues Aib2, K17, Aib20 and Aib29, where the structures of these amino acid residues have been expanded:

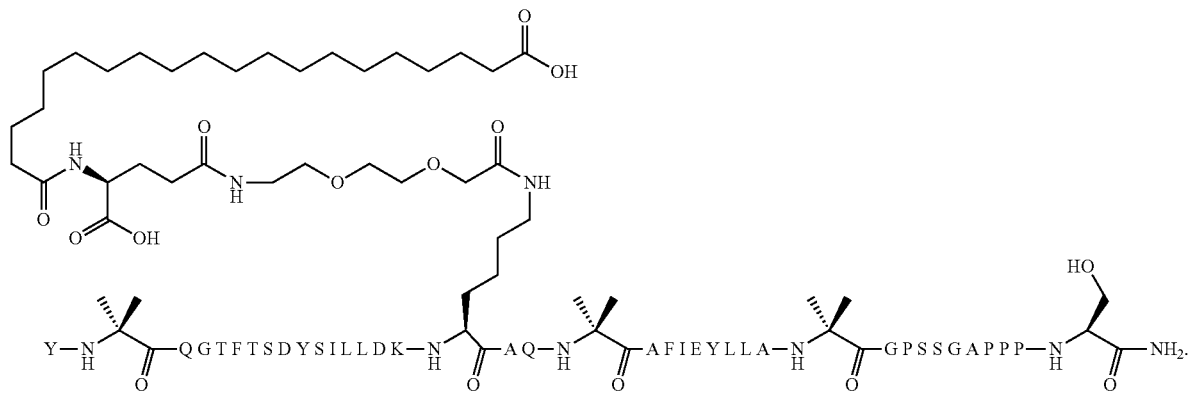

Similar processes to those described above for Example 1 are used to synthesize the peptide backbone, conjugate the fatty acid-linker moiety, examine the purity and confirm the molecular weight of Example 4.

EXAMPLE 5

Example 5 is a compound represented by the following description:

```
                                                    (SEQ ID NO: 10)
Y-Aib-QGTFTSDYSI-αMeL-LDKK((2-[2-(2-amino-
ethoxy)-ethoxy]-acetyl)₂-(γGlu)-CO—(CH₂)₁₈—CO₂H)
AAQAFIEYLLE-Aib-GPSSGAPPPS-NH₂.
```

Below is a depiction of the structure of Example 5 (SEQ ID NO:10) using the standard single letter amino acid codes with the exception of residues Aib2, αMeL13, K17, and Aib29, where the structures of these amino acid residues have been expanded:

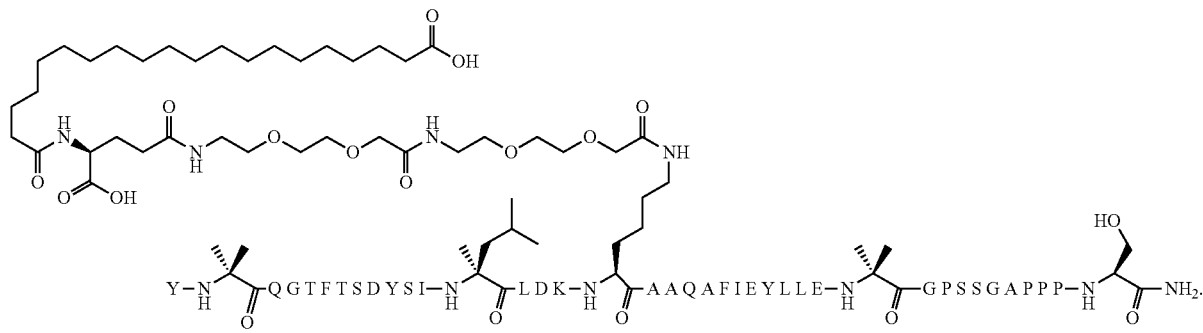

Similar processes to those described above for Example 1 are used to synthesize the peptide backbone, conjugate the fatty acid-linker moiety, examine the purity and confirm the molecular weight of Example 5.

EXAMPLE 6

Example 6 is a compound represented by the following description:

```
                                          (SEQ ID NO: 11)
Y-Aib-QGTFTSDYSI-αMeL-LDKK((2-[2-(2-aminoethoxy)-ethoxy]-acetyl)2-(γGlu)-CO—(CH2)18—CO2H)

AAQAFIEYLLEGGPSSGAPPPS-NH2.
```

Below is a depiction of the structure of Example 6 (SEQ ID NO:11) using the standard single letter amino acid codes with the exception of residues Aib2, αMeL13, and K17, where the structures of these amino acid residues have been expanded:

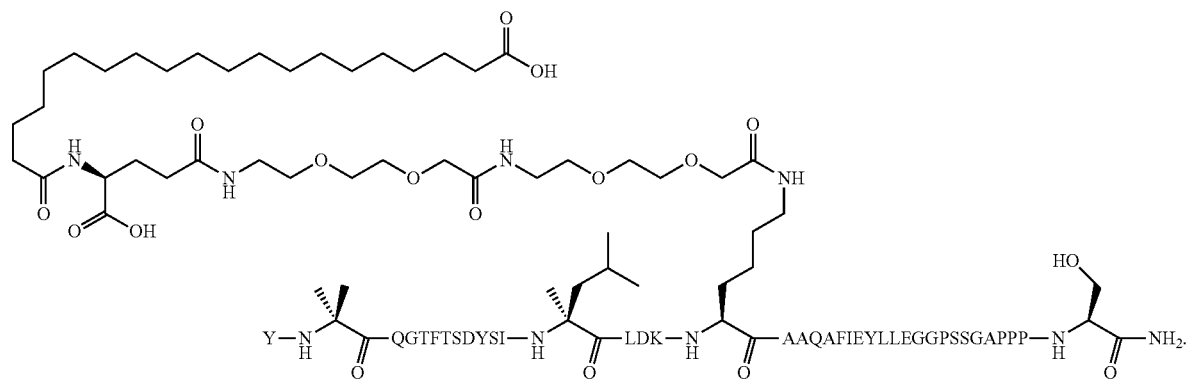

Similar processes to those described above for Example 1 are used to synthesize the peptide backbone, to conjugate the fatty acid-linker moiety, to examine the purity, and to confirm the molecular weight of Example 6.

EXAMPLE 7

Example 7 is a compound represented by the following description:

```
                                          (SEQ ID NO: 12)
Y-Aib-QGTFTSDYSI-αMeL-LDKK((2-[2-(2-aminoethoxy)-ethoxy]-acetyl)2-(γGlu)-CO—(CH2)18—CO2H)

AQHAFIEYLLEGGPSSGAPPPS-NH2.
```

Below is a depiction of the structure of Example 7 (SEQ ID NO:12) using the standard single letter amino acid codes with the exception of residues Aib2, αMeL13 and K17, where the structures of these amino acid residues have been expanded:

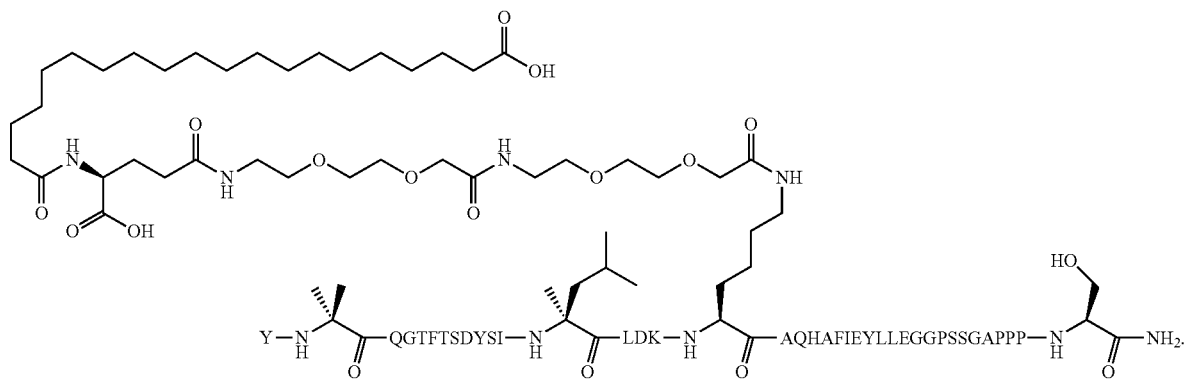

Similar processes to those described above for Example 1 are used to synthesize the peptide backbone, to conjugate the fatty acid-linker moiety, to examine the purity, and to confirm the molecular weight of Example 7.

EXAMPLE 8

Example 8 is a compound represented by the following description:

(SEQ ID NO: 13)
Y-Aib-QGTFTSDYSILLDKK((2-[2-(2-amino-ethoxy)-ethoxy]-acetyl)$_2$-(γGlu)-CO—(CH$_2$)$_{18}$—CO$_2$H)AQ-αMeK-AFIEYLLEGGPSSGAPPPS-NH$_2$.

Below is a depiction of the structure of Example 8 (SEQ ID NO:13) using the standard single letter amino acid codes with the exception of residues Aib2, K17 and αMeK20, where the structures of these amino acid residues have been expanded:

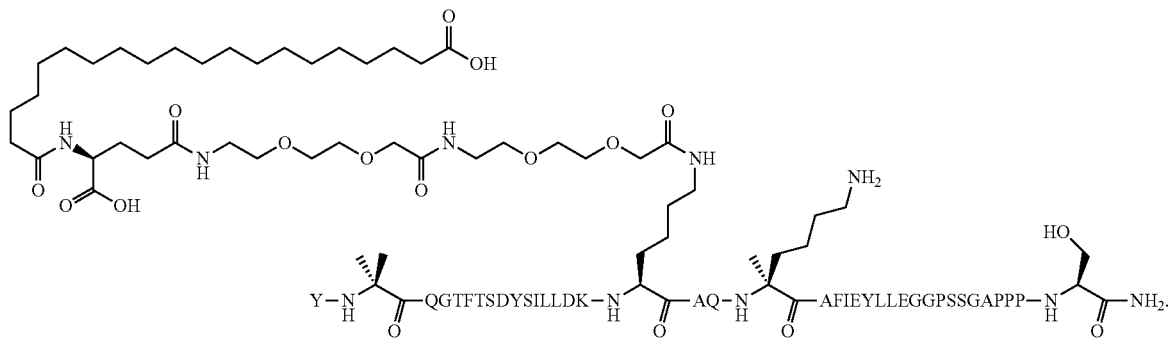

Similar processes to those described above for Example 1 are used to synthesize the peptide backbone, to conjugate the fatty acid-linker moiety, to examine the purity, and to confirm the molecular weight of Example 8.

EXAMPLE 9

Example 9 is a compound represented by the following description:

(SEQ ID NO: 14)
Y-Aib-QGTFTSDYSI-αMeL-LDKK((γGlu)$_2$-CO—(CH$_2$)$_{18}$—CO$_2$H)
AQHAFIEYLLEGGPSSGAPPPS-NH$_2$.

Below is a depiction of the structure of Example 9 (SEQ ID NO:14) using the standard single letter amino acid codes with the exception of residues Aib2, αMeL13 and K17, where the structures of these amino acid residues have been expanded:

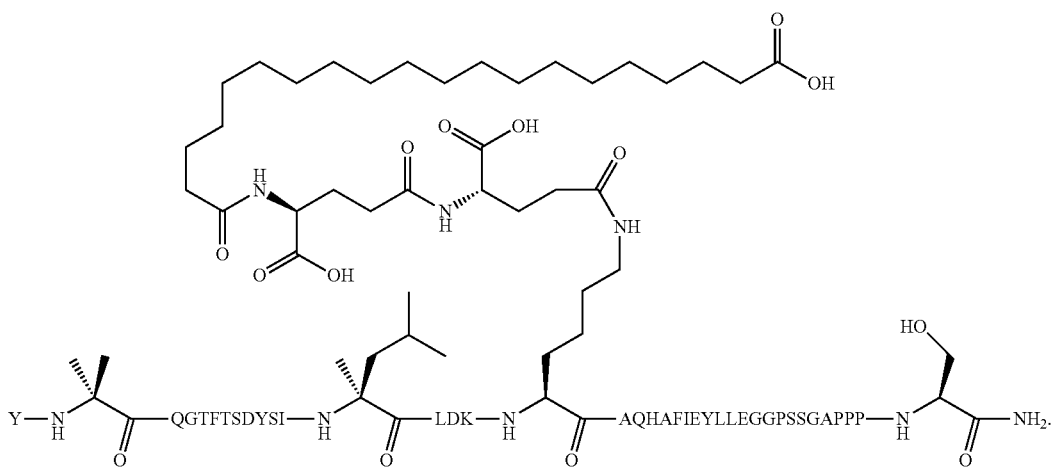

Similar processes to those described above for Example 1 are used to synthesize the peptide backbone, to conjugate the fatty acid-linker moiety, to examine the purity, and to confirm the molecular weight of Example 9.

EXAMPLE 10

Example 10 is a compound represented by the following description:

(SEQ ID NO: 15)
Y-Aib-QGTFTSDYSI-αMeL-LDKK((2-[2-(2-amino-ethoxy)-ethoxy]-acetyl)-(γGlu)-CO—(CH$_2$)$_{18}$—CO$_2$H)AQHAFIEYLLEGGPSSGAPPPS-NH$_2$.

Below is a depiction of the structure of Example 10 (SEQ ID NO:15) using the standard single letter amino acid codes with the exception of residues Aib2, αMeL13 and K17, where the structures of these amino acid residues have been expanded:

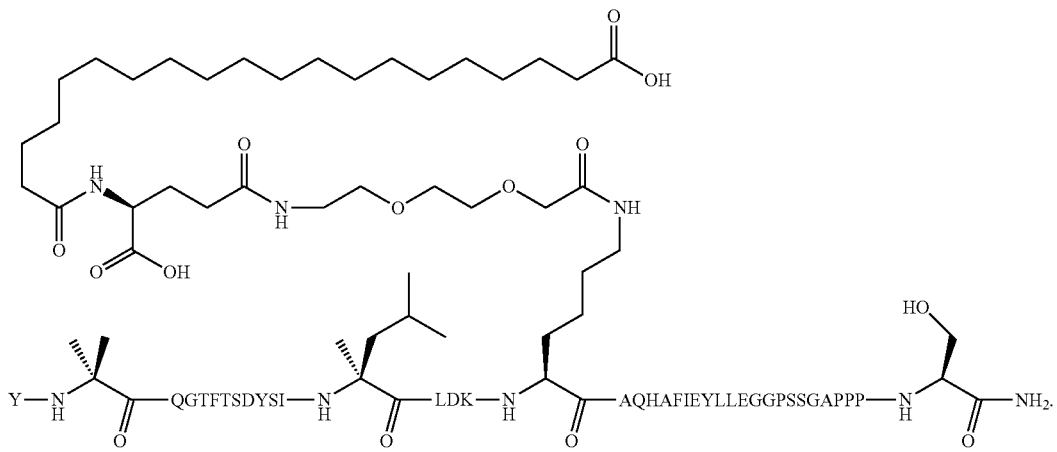

Similar processes to those described above for Example 1 are used to synthesize the peptide backbone, to conjugate the fatty acid-linker moiety, to examine the purity, and to confirm the molecular weight of Example 10.

EXAMPLE 11

Example 11 is a compound represented by the following description:

(SEQ ID NO: 16)
Y-Aib-QGTFTSDYSI-αMeL-LDKK((2-[2-(2-amino-ethoxy)-ethoxy]-acetyl)$_2$-(γGlu)-CO-(CH$_2$)$_{18}$-CO$_2$H)AQ-Aib-AFIEYLLEGGPSSGAPPPS-NH$_2$.

Below is a depiction of the structure of Example 11 (SEQ ID NO:16) using the standard single letter amino acid codes with the exception of residues Aib2, αMeL13, K17 and Aib20, where the structures of these amino acid residues have been expanded:

Similar processes to those described above for Example 1 are used to synthesize the peptide backbone, to conjugate the fatty acid-linker moiety, to examine the purity, and to confirm the molecular weight of Example 11.

EXAMPLE 12

Example 12 is a compound represented by the following description:

(SEQ ID NO: 17)
Y-Aib-QGTFTSDYSI-αMeL-LDKK((2-[2-(2-amino-ethoxy)-ethoxy]-acetyl)-(γGlu)-CO-(CH$_2$)$_{18}$-CO$_2$H)AQ-Aib-AFIEYLLEGGPSSGAPPPS-NH$_2$.

Below is a depiction of the structure of Example 12 (SEQ ID NO:17) using the standard single letter amino acid codes with the exception of residues Aib2, αMeL13, K17 and Aib20, where the structures of these amino acid residues have been expanded:

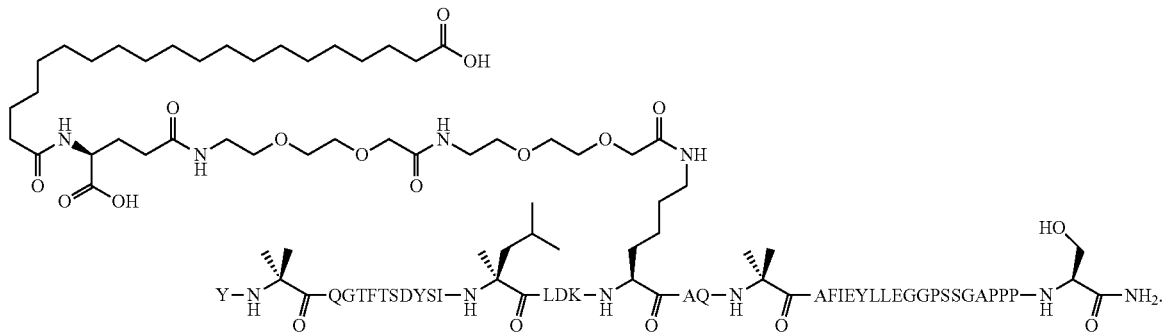

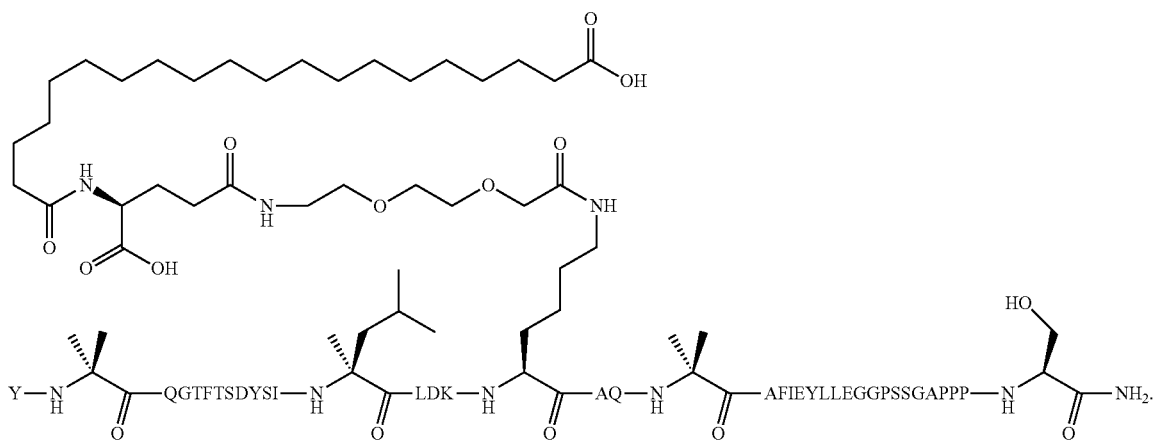

Similar processes to those described above for Example 1 are used to synthesize the peptide backbone, to conjugate the fatty acid-linker moiety, to examine the purity, and to confirm the molecular weight of Example 12.

EXAMPLE 13

Example 13 is a compound represented by the following description:

(SEQ ID NO: 18)
Y-Aib-QGTFTSDYSI-αMeL-LDKK((2-[2-(2-amino-ethoxy)-ethoxy]-acetyl)-(γGlu)-CO—(CH$_2$)$_{18}$—CO$_2$H)-AQ-Aib-AFIEYLLE-Aib-GPSSGAPPPS-NH$_2$.

Below is a depiction of the structure of Example 13 (SEQ ID NO:18) using the standard single letter amino acid codes with the exception of residues Aib2, αMeL13, K17, Aib20 and Aib29, where the structures of these amino acid residues have been expanded:

Similar processes to those described above for Example 1 are used to synthesize the peptide backbone, to conjugate the fatty acid-linker moiety, to examine the purity, and to confirm the molecular weight of Example 13.

EXAMPLE 14

Example 14 is a compound represented by the following description:

(SEQ ID NO: 19)
Y-Aib-QGTFTSDYSI-αMeL-LDKK((2-[2-(2-amino-ethoxy)-ethoxy]-acetyl)-(γGlu)-CO—(CH$_2$)$_{18}$—CO$_2$H)AQ-Aib-AFIEYLLE-Aib-GPSS-Aib-APPPS-NH$_2$.

Below is a depiction of the structure of Example 14 (SEQ ID NO:19) using the standard single letter amino acid codes with the exception of residues Aib2, αMeL13, K17, Aib20, Aib29 and Aib34 where the structures of these amino acid residues have been expanded:

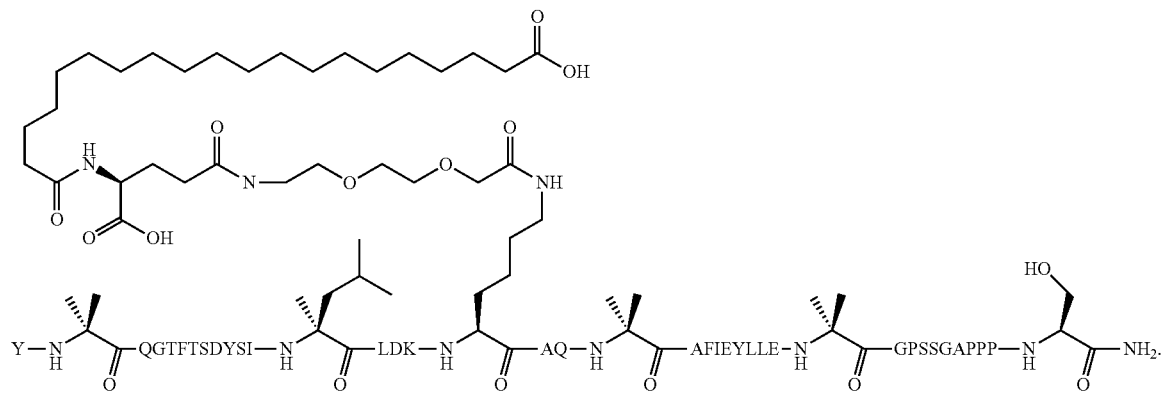

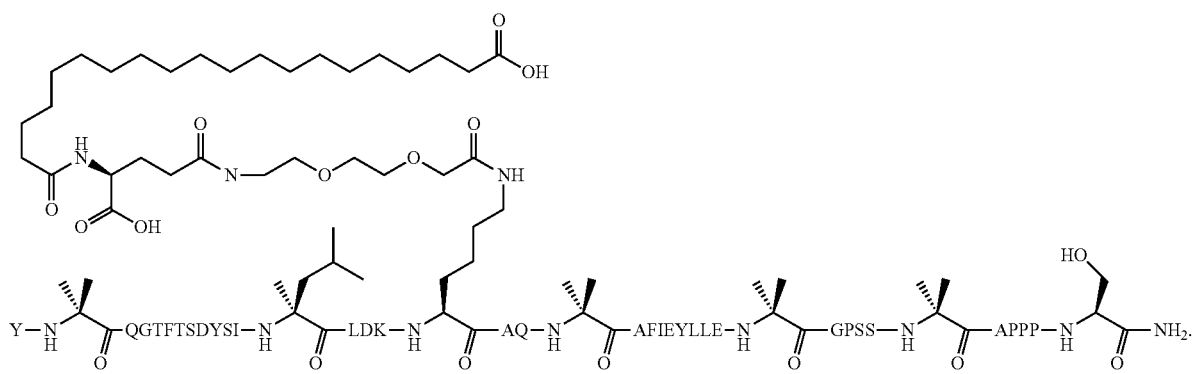

Similar processes to those described above for Example 1 are used to synthesize the peptide backbone, to conjugate the fatty acid-linker moiety, to examine the purity, and to confirm the molecular weight of Example 14.

Similar processes to those described above for Example 1 are used to synthesize the peptide backbone, to conjugate the fatty acid-linker moiety, to examine the purity, and to confirm the molecular weight of Example 15.

EXAMPLE 15

Example 15 is a compound represented by the following description:

```
                                              (SEQ ID NO: 20)
Y-Aib-QGTFTSDYSILLDKK((2-[2-(2-amino-ethoxy)-
ethoxy]-acetyl)_2-(γGlu)-CO-(CH_2)_18-CO_2H)AQ-Aib-AFI
EYLLA-Aib-GPSSGAPPPS-NH_2.
```

Below is a depiction of the structure of Example 15 (SEQ ID NO:20) using the standard single letter amino acid codes with the exception of residues Aib2, K17, Aib20 and Aib29, where the structures of these amino acid residues have been expanded:

EXAMPLE 16

Example 16 is a compound represented by the following description:

```
                                              (SEQ ID NO: 21)
Y-Aib-QGTFTSDYSILLDKK((2-[2-(2-amino-ethoxy)-
ethoxy]-acetyl)_2-(γGlu)-CO-(CH_2)_18-CO_2H)AQ-Aib-AFIE
YLLEGGPSSGAPPPS-NH_2.
```

Below is a depiction of the structure of Example 16 (SEQ ID NO:21) using the standard single letter amino acid codes with the exception of residues Aib2, K17, and Aib20, where the structures of these amino acid residues have been expanded:

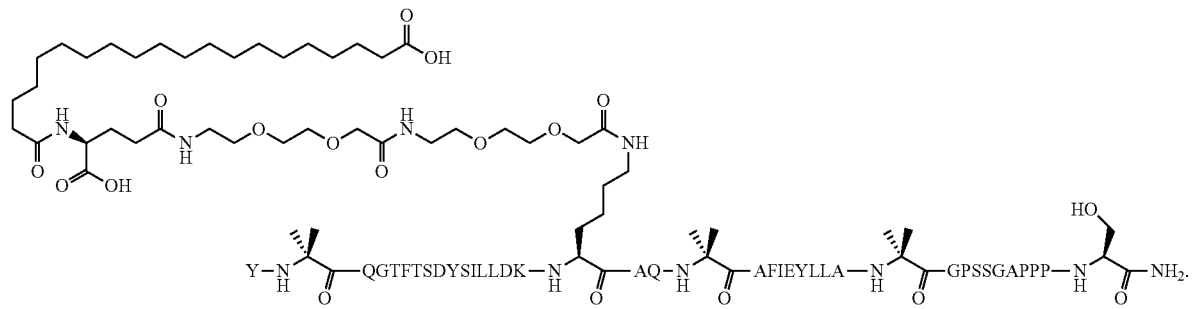

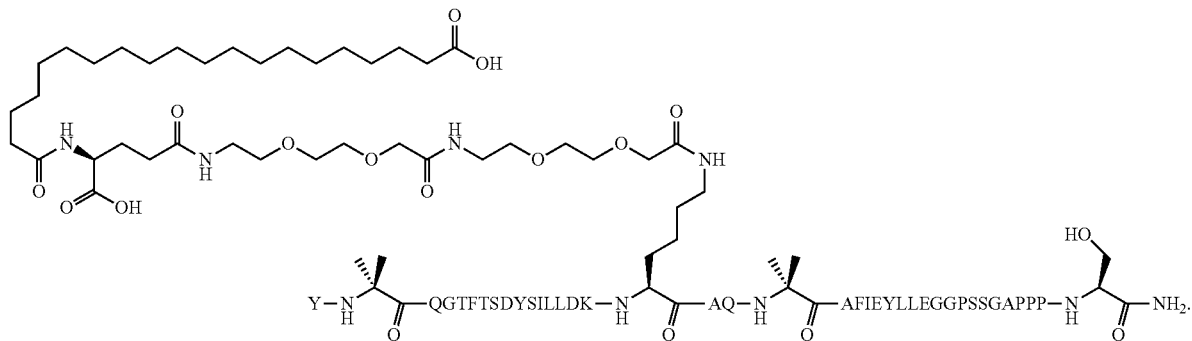

Similar processes to those described above for Example 1 are used to synthesize the peptide backbone, to conjugate the fatty acid-linker moiety, to examine the purity, and to confirm the molecular weight of Example 16.

EXAMPLE 17

Example 17 is a compound represented by the following description:

```
                                              (SEQ ID NO: 22)
Y-Aib-QGTFTSDYSILLDKK((2-[2-(2-amino-ethoxy)-
ethoxy]-acetyl)₂-(γGlu)-CO-(CH₂)₁₈-CO₂H)AQ-Aib-AFIE
YLLE-Aib-GPSSGAPPPS-NH₂.
```

Below is a depiction of the structure of Example 17 (SEQ ID NO:22) using the standard single letter amino acid codes with the exception of residues Aib2, K17, Aib20 and Aib29, where the structures of these amino acid residues have been expanded:

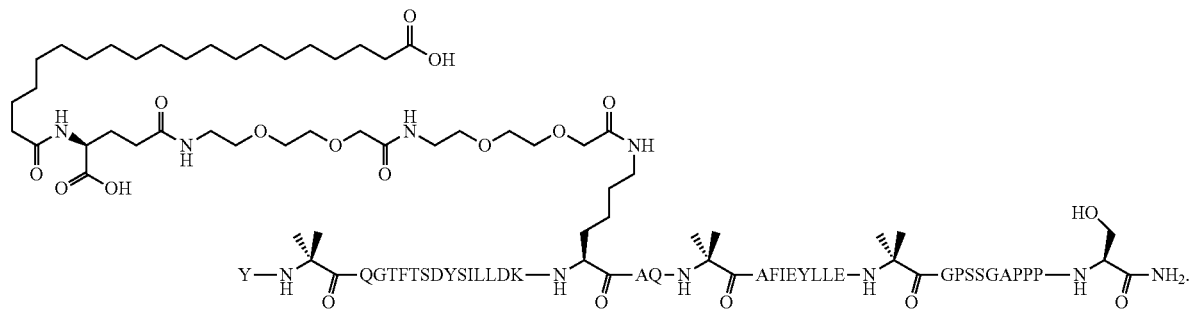

Similar processes to those described above for Example 1 are used to synthesize the peptide backbone, to conjugate the fatty acid-linker moiety, to examine the purity, and to confirm the molecular weight of Example 17.

EXAMPLE 18

Example 18 is a compound represented by the following description:

```
                                            (SEQ ID NO: 23)
Y-Aib-QGTFTSDYSILLDKK((2-[2-(2-amino-ethoxy)-
ethoxy]-acetyl)-(γGlu)-CO-(CH₂)₁₈-CO₂H)AQ-Aib-AFIE
YLLEGGPSSGAPPPS-NH₂.
```

Below is a depiction of the structure of Example 18 (SEQ ID NO:23) using the standard single letter amino acid codes with the exception of residues Aib2, K17, and Aib20, where the structures of these amino acid residues have been expanded:

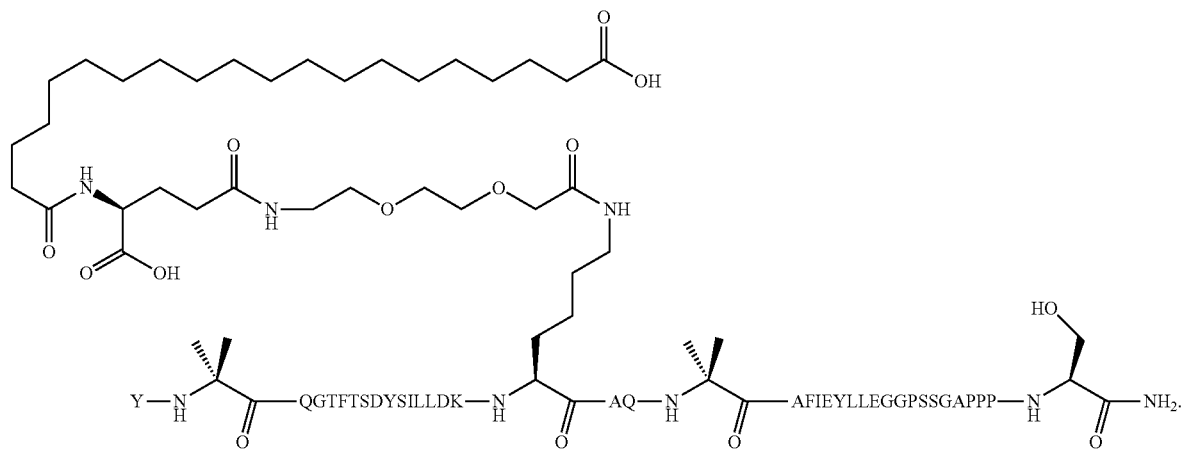

Similar processes to those described above for Example 1 are used to synthesize the peptide backbone, to conjugate the fatty acid-linker moiety, to examine the purity, and to confirm the molecular weight of Example 18.

EXAMPLE 19

Example 19 is a compound represented by the following description:

```
                                            (SEQ ID NO: 24)
Y-Aib-QGTFTSDYSILLDKK((2-[2-(2-amino-ethoxy)-
ethoxy]-acetyl)-(γGlu)₂-CO-(CH₂)₁₈-CO₂H)AQ-Aib-AFIE
YLLE-Aib-GPSSGAPPPS-NH₂.
```

Below is a depiction of the structure of Example 19 (SEQ ID NO:24) using the standard single letter amino acid codes with the exception of residues Aib2, K17, Aib20 and Aib29, where the structures of these amino acid residues have been expanded:

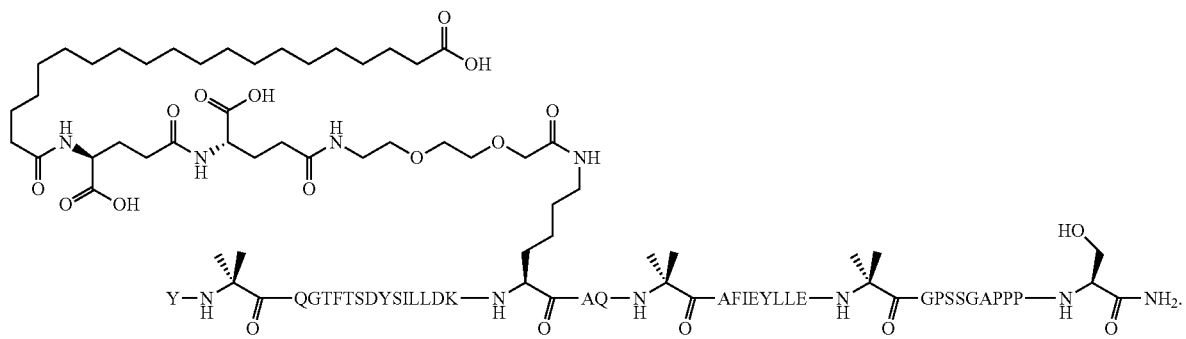

Similar processes to those described above for Example 1 are used to synthesize the peptide backbone to conjugate the fatty acid-linker moiety, to examine the purity, and to confirm the molecular weight of Example 19.

EXAMPLE 20

Example 20 is a compound represented by the following description:

(SEQ ID NO: 25)
Y-Aib-QGTFTSDYSILLDKK((2-[2-(2-amino-ethoxy)-ethoxy]-acetyl)-(γGlu)-CO—(CH$_2$)$_{18}$—CO$_2$H)AQ-Aib-AFIEYLLE-Aib-GPSSGAPPPS-NH$_2$.

Below is a depiction of the structure of Example 20 (SEQ ID NO:25) using the standard single letter amino acid codes with the exception of residues Aib2, K17, Aib20 and Aib29, where the structures of these amino acid residues have been expanded:

Similar processes to those described above for Example 1 are used to synthesize the peptide backbone, to conjugate the fatty acid-linker moiety, to examine the purity, and to confirm the molecular weight of Example 20.

In Vitro Function

Binding Affinity:

Radioligand competition binding assays are run to determine the equilibrium dissociation constant for exemplary compounds and comparator molecules. Such assay use scintillation proximity assay (SPA) methods and membranes prepared from transfected HEK293 cells overexpressing the human GIP receptor (GIPR), GLP-1 receptor (GLP-1R) or human glucagon receptor (GcgR).

The assays are performed in the presence of bacitracin as a non-specific blocking agent to prevent acylated moieties of test analogs from binding to protein components used in standard assay buffers (e.g., albumin).

Competition curves are plotted as the percent specific inhibition (y-axis) versus log concentration of compound (x-axis) and analyzed using a four parameter nonlinear regression fit with variable slope (ABase or Genedata). $K_i$ values are calculated according to the equation $K_i=IC_{50}/(1+(D/K_d))$, where $IC_{50}$ is the concentration of compound resulting in 50% inhibition of binding, D is the concentration of radioligand used in the assay, and $K_d$ is the equilibrium dissociation constant for the receptor and the radioligand, determined from saturation binding analysis (shown in Table 1 below).

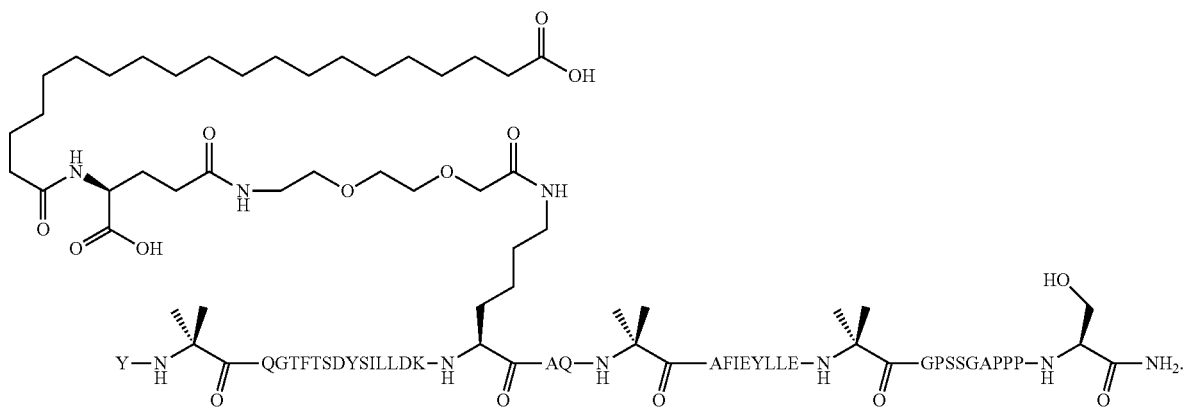

TABLE 1

Equilibrium Dissociation Constants ($K_d$) Determined from Saturation Binding Analysis.

| $K_d$, nM | | |
|---|---|---|
| GLP-1R | GcgR | GIPR |
| 1.2 | 3.9 | 0.14 |

$K_i$ values of exemplary analogs and comparator molecules are shown in Table 2.

TABLE 2

In Vitro Binding Affinity ($K_i$) of Examples and Comparators for Human GIPR, GLP-1R and GcgR.

| | $K_i$, nM (SEM, n) | | |
|---|---|---|---|
| Molecule | GcgR | GIPR | GLP-1R |
| hGcg | 3.1 (0.5, 4) | | |
| hGIP | | 0.12 (0.02, 4) | |
| hGLP-1 | | | 1.2 (0.2, 4) |
| Example 1 | 8.41 (2.71, 5) | 0.0469 (0.00558, 4/5) | 2.64 (0.501, 5) |
| Example 2 | 3.71 (1.49, 2) | 0.0665 (0.0377, 2) | 4.50 (0.735, 2) |
| Example 3 | 12.0 (2.74, 4) | 0.0446 (0.00838, 4) | 6.06 (0.849, 4) |
| Example 4 | 2.55 (0.411, 4) | 0.0374 (0.0137, 4) | 3.54 (0.503, 6) |
| Example 5 | 0.422 (0.0887, 3) | 0.179 (0.0466, 3) | 36.7 (8.99, 3) |
| Example 6 | 0.835 (0.369, 3) | 0.249 (0.0369, 3) | 36.7 (10.5, 3) |
| Example 7 | 16.3 (2.37, 5) | 0.110 (0.0206, 5) | 21.4 (3.53, 5) |
| Example 8 | 30.4 (38.9, 3) | 0.0958 (0.0295, 3) | 29.4 (29.8, 3) |
| Example 9 | 8.27 (0.855, 4) | 0.126 (0.0274, 4) | 11.5 (1.85, 4) |
| Example 10 | 7.37 (1.38, 4) | 0.118 (0.0363, 4) | 12.0 (2.75, 4) |
| Example 11 | 10.8 (1.11, 4) | 0.0890 (0.0369, 3/4) | 9.97 (1.53, 4) |
| Example 12 | 5.60 (0.796, 4) | 0.0570 (0.00322, 4) | 7.17 (1.68, 4) |
| Example 13 | 1.91 (0.128, 3) | 0.0452 (0.00297, 3) | 6.43 (1.89, 5) |
| Example 14 | 2.64 (0.231, 4) | 0.0350 (0.00326, 4) | 6.27 (1.12, 6) |
| Example 15 | 4.56 (2.68, 2) | 0.0972 (n = 1/2) | 5.80 (1.80, 3) |
| Example 16 | 11.5 (1.97, 5) | 0.106 (0.0182, 5) | 16.1 (2.30,6) |
| Example 17 | 5.81 (0.875, 3) | 0.0895 (0.0290, 3) | 10.2 (1.74, 3) |
| Example 18 | 5.71 (0.588, 4) | 0.0835 (0.0128, 4) | 8.06 (2.04, 4) |
| Example 19 | 5.20 (0.572, 3) | 0.0789 (0.0261, 3) | 12.0 (2.07, 3) |
| Example 20 | 3.76 (0.397, 3) | 0.109 (0.0247, 3) | 9.23 (2.14, 3) |

NOTE: A qualifier (>) indicates the data did not reach 50% inhibition relative to maximum binding, whereby the $K_i$ was calculated using the highest concentration tested in the assay. n = 1/x means that only one value out of the total number of replicates (x) is used to express the mean. SEM is only calculated when n = 2 or greater non-qualified results exist.

As seen in Table 2, exemplary analogs have binding affinity at each of the GIP, GLP-1 and glucagon receptors.

Functional Activity:

Functional activity is determined in GIP-R-GLP-1R- and GcgR-expressing HEK-293 clonal cell lines. Each receptor over-expressing cell line is treated with peptide (20 point CRC, 2.75-fold Labcyte Echo direct dilution) in DMEM (Gibco Cat #31053) supplemented with 1× GlutaMAX™ (Gibco Cat #35050), 0.25% FBS (Fetal Bovine Serum, Gibco Cat #26400), 0.05% fraction V BSA (Bovine Serum Albumin, Gibco Cat #15260), 250 µM IBMX and 20 mM HEPES (Gibco Cat #15630) in a 20 µl assay volume.

After a 60-minute incubation at room temperature, the resulting increase in intracellular cAMP is quantitatively determined using the CisBio cAMP Dynamic 2 HTRF Assay Kit (62AM4PEJ). Briefly, cAMP levels within the cell are detected by adding the cAMP-d2 conjugate in cell lysis buffer followed by the antibody anti-cAMP-Eu$^{3+}$-Cryptate, also in cell lysis buffer. The resulting competitive assay is incubated for at least 60 minutes at room temperature and then detected using a PerkinElmer Envision® Instrument with excitation at 320 nm and emission at 665 nm and 620 nm. Envision units (emission at 665 nm/620 nm*10,000) are inversely proportional to the amount of cAMP present and were converted to nM cAMP per well using a cAMP standard curve.

The amount of cAMP generated (nM) in each well is converted to a percent of the maximal response observed with either human GLP-1(7-36)NH$_2$, human Gcg, or human GIP(1-42)NH$_2$. A relative $EC_{50}$ value is derived by non-linear regression analysis using the percent maximal response vs. the concentration of peptide added, fitted to a four-parameter logistic equation.

Data for exemplary analogs and hGIP(1-42)NH$_2$, hGLP-1(7-36)NH$_2$ and hGcg are shown in Table 3 below.

TABLE 3

Functional cAMP Potency ($EC_{50}$) for Exemplary
Analogs and Comparators in the Presence of FBS and BSA.

cAMP $EC_{50}$, nM (SEM, n)

| | GcgR | GIPR | GLP-1R |
|---|---|---|---|
| hGcg | 0.0125 (0.000280014, 112) | | |
| gGIP amide | | 0.133 (0.0082, 60) | |
| hGLP-1 amide | | | 0.0591 (0.00091, 113) |
| Example 1 | 2.54 (0.199, n = 6) | 0.914 (0.0915, 6) | 7.49 (1.02, 6) |
| Example 2 | 2.66 (0.175, 5) | 2.19 (0.392, 5) | 12.8 (2.50, 5) |
| Example 3 | 8.03 (0.997, 6) | 1.91 (0.205, 6) | 12.9 (1.58, 6) |
| Example 4 | 2.49 (0.371, 7) | 1.55 (0.245, 7) | 10.4 (1.80, 7) |
| Example 5 | 1.47 (0.171, 6) | 4.86 (0.682, 6) | 22.3 (3.78, 6) |
| Example 6 | 1.99 (0.201, 6) | 7.41 (0.667, 6) | 21.2 (2.02, 6) |
| Example 7 | 14.2 (2.24, 6) | 4.38 (0.750, 6) | 15.5 (2.40, 6) |
| Example 8 | 6.24 (0.673, 6) | 2.23 (0.164, 6) | 9.39 (0.959, 6) |
| Example 9 | 6.32 (0.290, 4) | 4.17 (0.695, 4) | 9.76 (1.98, 4) |
| Example 10 | 8.42 (1.17, 4) | 4.30 (0.987, 4) | 19.3 (1.52, 4) |
| Example 11 | 11.9 (0.727, 6) | 1.50 (0.124, 6) | 10.3 (0.808, 6) |
| Example 12 | 6.61 (0.512, 6) | 2.24 (0.303, 6) | 12.4 (1.41, 6) |
| Example 13 | 3.61 (0.197, 8) | 1.76 (0.126, 8) | 12.2 (1.00, 8) |
| Example 14 | 4.05 (0.255, 7) | 1.55 (0.165, 7) | 14.4 (1.71, 7) |
| Example 15 | 5.92 (1.10, 4) | 1.47 (0.264, 4) | 10.7 (1.85, 4) |
| Example 16 | 13.2 (1.93, 6) | 4.37 (0.589, 6) | 19.0 (2.39, 6) |
| Example 17 | 8.05 (1.26, 3) | 2.38 (0.212, 3) | 18.4 (3.75, 3) |
| Example 18 | 5.71 (0.256, 4) | 5.89 (1.05, 4) | 16.1 (2.61, 4) |
| Example 19 | 8.45 (0.828, 3) | 3.13 (0.179, 3) | 24.4 (2.85, 3) |
| Example 20 | 3.97 (0.284, 3) | 3.70 (1.02, 3) | 20.6 (5.10, 3) |

NOTE: $EC_{50}$ determination of human GLP-1(7-36)$NH_2$ at human GLP-1R, human Gcg at human GcgR, and human GIP(1-42)$NH_2$ at human GIP-R: the peptide concentration ranges were 448 pM to 99.5 nM. $EC_{50}$ determination of Examples at human GLP-1R, human GcgR, and human GIP-R: the peptide concentration ranges were 51.5 fM to 11.4 µM.

As seen in Table 3, in the presence of FBS and BSA, exemplary analogs have agonist activities as determined by human GIP-R, GLP-1R, and GcgR cAMP cAMP assays, which are lower than the native ligands.

An additional set of cAMP assays are conducted in HEK293 cells expressing the human GLP-1, GIP and glucagon receptors. Using homogeneous time resolved fluorescence methods, assays are conducted to determine the intrinsic potency of exemplary analogs and comparator molecules performed in the presence of casein (instead of serum albumin) as a nonspecific blocker, which does not interact with the fatty acid moieties of the analyzed molecules.

Intracellular cAMP levels are determined by extrapolation using a standard curve. Dose response curves of compounds are plotted as the percentage of stimulation normalized to minimum (buffer only) and maximum (maximum concentration of each control ligand) values and analyzed using a four parameter non-linear regression fit with a variable slope (Genedata Screener 13). $EC_{50}$ is the concentration of compound causing half-maximal simulation in a dose response curve.

Data are provided below in Table 4.

TABLE 4

Functional Activation of hGLP-1R, hGIPR, hGcgR in the Presence of 0.1% Casein.

cAMP $EC_{50}$, nM (SEM, n)

| | GcGR | GIPR | GLP-1R |
|---|---|---|---|
| hGcg | 0.0119 (0.00356, 163) | | |
| hGIP amide | | 0.154 (0.037, 118) | |
| gGLP-1 amide | | | 0.063 (0.022, 197) |
| Example 1 | 0.114 (0.0203, 5) | 0.0523 (0.0112, 5) | 0.153 (0.0132, 12) |
| Example 2 | 0.0553 (0.00975, 4) | 0.0474 (0.00485, 4) | 0.207 (0.0213, 6) |
| Example 3 | 0.152 (0.0147, 7) | 0.0376 (0.00284, 7) | 0.107 (0.0108, 7) |
| Example 4 | 0.0674 (0.00532, 15) | 0.0648 (0.00507, 14) | 0.180 (0.0144, 17) |
| Example 5 | 0.0226 (0.00304, 10) | 0.0757 (0.0127, 5) | 0.147 (0.0204, 7) |
| Example 6 | 0.0282 (0.00409, 7) | 0.274 (0.0377, 7) | 0.142 (0.0127, 10) |
| Example 7 | 0.180 (0.0190, 6) | 0.0798 (0.0111, 6) | 0.109 (0.0134, 5) |
| Example 8 | 0.120 (0.0210, 5) | 0.114 (0.0101, 4) | 0.117 (0.0151, 7) |
| Example 9 | 0.139 (0.0281, 5) | 0.0522 (0.00816, 4) | 0.0931 (0.00852, 8) |
| Example 10 | 0.123 (0.00784, 15) | 0.0928 (0.00721, 16) | 0.143 (0.0103, 12) |
| Example 11 | 0.205 (0.0175, 11) | 0.0425 (0.00744, 12) | 0.123 (0.0119, 13) |
| Example 12 | 0.122 (0.00931, 15) | 0.0529 (0.00394, 18) | 0.162 (0.0100, 18) |
| Example 13 | 0.0815 (0.00835, 12) | 0.0391 (0.00315, 14) | 0.125 (0.00961, 13) |
| Example 14 | 0.0876 (0.00687, 17/18) | 0.0356 (0.00242, 20) | 0.146 (0.0108, 17) |
| Example 15 | 0.131 (0.0141, 10) | 0.0689 (0.00730, 9) | 0.253 (0.0197, 9) |
| Example 16 | 0.174 (0.00882, 22) | 0.114 (0.0100, 20) | 0.157 (0.0105, 20) |
| Example 17 | 0.135 (0.00643, 12) | 0.0439 (0.00457, 11) | 0.153 (0.0135, 10) |

TABLE 4-continued

Functional Activation of hGLP-1R, hGIPR, hGcgR in the Presence of 0.1% Casein.

| | cAMP EC$_{50}$, nM (SEM, n) | | |
|---|---|---|---|
| | GcGR | GIPR | GLP-1R |
| Example 18 | 0.0861 (0.00631, 16) | 0.123 (0.00954, 13) | 0.141 (0.00862, 13) |
| Example 19 | 0.0874 (0.0317, 2) | 0.0455 (0.00516, 2) | 0.143 (0.0187, 3) |
| Example 20 | 0.0641 (0.00369, 12) | 0.0572 (0.00527, 11) | 0.149 (0.00937, 11) |

As seen in Table 4, exemplary analogs stimulate cAMP from human GIP, GLP-1 and glucagon receptors in the presence of 0.1% casein.

In Vivo Studies

Pharmacokinetics in Male Sprague Dawley Rats:

The pharmacokinetics of the exemplary analogs are evaluated following a single subcutaneous administration of 100 nM/kg to male Sprague Dawley rats. Blood samples are collected over 120 hours, and resulting individual plasma concentrations are used to calculate pharmacokinetic parameters. Peptide plasma (K$_3$ EDTA) concentrations are determined using a qualified LC/MS method that measured the intact mass of the analog. Each peptide and an analog as an internal standard are extracted from 100% specie specified plasma using methanol with 0.1% formic acid. A Thermo Q-Exactive, High Resolution Instrument, and a Thermo Easy Spray PepMap are combined for LC/MS detection. Mean pharmacokinetic parameters are shown in Table 5.

TABLE 5

Mean Pharmacokinetic Parameters of Peptides Following a Single Subcutaneous Administration of 100 nMol/kg to Male Sprague Dawley Rats.

| | T$_{1/2}$ (hr) | T$_{max}$ (hr) | C$_{max}$/D (kg*nmol/L/nmol) | AUCINF_D_obs (hr*kg*nmol/L/nmol) | Cl/F (mL/hr/Kg) |
|---|---|---|---|---|---|
| Example 1 | 11.7 | 8 | 3.5 | 95.7 | 10.4 |
| Example 3 | 19.2 | 16 | 2.5 | 146 | 6.9 |
| Example 4 | 19.9 | 16 | 2.9 | 140 | 7.2 |
| Example 10 | 23.4 | 24 | 3.1 | 203.5 | 4.9 |
| Example 11 | 24.3 | 20 | 3.7 | 215.1 | 4.7 |
| Example 12 | 26.5 | 24 | 3.7 | 197.1 | 5.1 |
| Example 13 | 21.7 | 20 | 3.8 | 205.7 | 4.9 |
| Example 16 | 29.1 | 20 | 3.8 | 274.9 | 3.6 |
| Example 18 | 34.8 | 24 | 5.0 | 284.3 | 3.6 |

Abbreviations:
T$_{1/2}$ = half-life,
T$_{max}$ = time to maximal concentration,
C$_{max}$ = maximal plasma concentration,
AUCINF_D_obs = AUCinf divided by dose,
CL/F = clearance/bioavailability.
NOTE: Data are the mean, where n = 3/group.

As seen in Table 5, exemplary analogs demonstrate an extended pharmacokinetic profile.

In Vivo Effect on Insulin Secretion in Male Wistar Rats:

An intravenous glucose tolerance test (ivGTT) in rats (male Wistar) is used to estimate insulinotropic potency of the exemplary analogs. The GLP-1 RA semaglutide is used as a positive control. Rats with surgically implanted cannulas in the jugular vein and carotid artery (Envigo, Indianapolis, Ind.; 280-320 grams) are housed one per cage in polycarbonate cages with filter tops. Rats are maintained on a 12-hour light-dark cycle at 21° C. and receive 2014 Teklad Global Diet (Envigo, Indianapolis) and deionized water ad libitum. Rats are randomized by body weight and dosed 1.5 mL/kg subcutaneous (sc) with exemplary analogs 16 hours prior to glucose administration, and then fasted. Stock concentrations of 211 nM of the exemplary analogs are diluted in Tris buffer pH 8.0 to 6.667 nMol/mL, 2.0 nMol/mL, 0.667 nMol/mL, 0.2 nMol/mL; doses tested are vehicle, 1, 3 and 10 nMol/kg, and, in some cases 0.3 and 30 nMol/kg. Semaglutide is used as positive control, and its insulinotropic effects are measured both in its own test (vehicle and 1, 3, 10 and 30 nMol/kg doses) and in connection with each run of the exemplary analogs (10 nMol/kg dose).

A time 0 blood sample is collected into EDTA tubes after which glucose is administered (0.5 mg/kg, 5 mL/kg). Blood samples are collected for glucose and insulin levels at time 2, 4, 6, 10, 20, and 30 minutes post intravenous administration of glucose. Plasma insulin is determined using an electrochemiluminescence assay (Meso Scale, Gaithersburg, Md.). Insulin area under the curve (AUC) is examined and compared to the vehicle control with n=6 animals per group.

Statistical analysis is performed using JMP with a one-way ANOVA followed by Dunnett's comparison to the vehicle control. Data are provided in Table 6 below.

TABLE 6

Effect of Vehicle, Semaglutide and Exemplary Analogs on Insulin Secretion During Intravenous Glucose Tolerance Test in Anesthetized Wistar Rats.

| | AUC$_{30min}$ of Insulin after a Bolus IV Glucose Dose (nmol/kg) | | | | Semaglutide |
|---|---|---|---|---|---|
| | 0 | 1 | 3 | 10 | (10 nmol/kg) |
| Ex. 1 | 11.1 ± 1.3 | 60.1 ± 10.3* | 53.8 ± 5.1* | 71.5 ± 6.1* | 51.86 +/− 6.7* |
| Ex. 3 | 12.6 ± 2.1 | 34.4 ± 2.9* | 47.5 ± 4.0* | 51.6 ± 5.4* | 45.6 +/− 6.6* |
| Ex. 4 | 13.7 ± 2.3 | 27.4 ± 3.0 | 52.9 ± 3.0* | 70.8 ± 8.4* | 44.7 +/− 3.7* |
| Ex. 11 | 11.3 ± 2.1 | 43.0 ± 6.8* | 59.2 ± 6.3* | 62.0 ± 4.6* | 55.1 +/− 9.0* |
| Ex. 12 | 9.3 ± 1.8 | 32.4 +/− 2.4* | 44.8 ± 2.3* | 53.6 ± 6.0*+ | 40.2 +/− 2.5* |

TABLE 6-continued

Effect of Vehicle, Semaglutide and Exemplary Analogs on Insulin
Secretion During Intravenous Glucose Tolerance Test in Anesthetized Wistar Rats.

| | AUC$_{30min}$ of Insulin after a Bolus IV Glucose Dose (nmol/kg) | | | | Semaglutide |
|---|---|---|---|---|---|
| | 0 | 1 | 3 | 10 | (10 nmol/kg) |
| Ex. 13 | 8.9 ± 1.2 | 25.8 ± 2.7 | 47.3 ± 8.0* | 70.6 ± 4.8* | 38.4 +/− 6.0* |
| Ex. 16 | 14.4 ± 2.1 | 18.9 ± 3.5 | 50.3 ± 4.2* | 50.1 ± 4.2* | 56.3 +/− 7.7* |
| Ex. 18 | 12.3 ± 2.0 | 27.6 ± 4.6 | 44.8 ± 8.3* | 57.3 ± 10.0* | 48.4 +/− 6.6* |

NOTE: results are expressed as Mean ± Standard Error of Means (SEM) of 6 rats per group. The statistical test is one-way ANOVA followed by Dunnett's *p < 0.05 compared to vehicle; +p < 0.05 compared to semaglutide.

As seen in Table 6, the exemplary analogs show dose-dependent increases in insulin secretion.

Studies in Diet-Induced Obese C57BL/6 Mice:

The exemplary incretin analogs as described herein are proposed as a treatment not only for diabetes but also for metabolic syndrome, which is a collection of co-morbidities (dyslipidemia, obesity, hepatic steatosis, etc.) associated with insulin resistance and diabetes. To investigate the effects of the exemplary analogs on parameters such as weight loss, metabolism, body composition and hepatic steatosis, they were dosed to C57BL/6 diet-induced obese (DIO) mice. These animals, although not diabetic, display insulin resistance, dyslipidemia and hepatic steatosis, all characteristics of metabolic syndrome, after being placed on a high-fat diet for 18 weeks.

Specifically, DIO male C57BL/6 mice 24 to 25 weeks old maintained on a calorie-rich diet are used in the following studies. Mice are individually housed in a temperature-controlled (24° C.) facility with 12-hour light/dark cycle (lights on 22:00) and free access to food (TD95217) and water. After a minimum of 2 weeks acclimation to the facility, the mice are randomized according to their body weight, so each experimental group of animals would have similar body weight. The body weights range from 40 to 51 g.

All groups contain 5-6 mice. Vehicle, exemplary analogs dissolved in vehicle (40 mM Tris-HCl at pH 8.0), and semaglutide dissolved in vehicle are administered by subcutaneous (SC) injection (10 mL/kg) to ad libitum fed DIO mice 30 to 90 minutes prior to the onset of the dark cycle every 3 days for 15 days. SC injections are made on Day 1, 4, 7, 10 and 13. Body weight and food intake are measured daily throughout the study.

Absolute changes in body weight are calculated by subtracting the body weight of the same animal prior to the first injection of vehicle, analog or semaglutide. On Days 0 and 15, total fat mass is measured by nuclear magnetic resonance (NMR) using an Echo Medical System Instrument (Houston, Tex.). On Day 15, animals are sacrificed prior to dark photoperiod, and the livers are removed and frozen. Liver triglycerides, determined from homogenates of livers collected at sacrifice, and plasma cholesterol are measured on a Hitachi Modular P clinical analyzer.

Data are presented as mean±SEM of 5-6 animals per group in Tables 7 and 8 below. Statistical analysis is performed using repeated measures ANOVA, followed by Dunnett's method for multiple comparisons. Significant differences are identified at p<0.05.

TABLE 7

Body Weight Change After Treatment with Exemplary Analogs After Fifteen Days.

| | Treatment Dose | | | | | |
|---|---|---|---|---|---|---|
| | 3 nmol/kg | | 10 nmol/kg | | 30 nmol/kg | |
| | Δ from vehicle (g) | % change | Δ from vehicle (g) | % change | Δ from vehicle (g) | % change |
| Ex. 1 | −5.42 ± 0.54 | −10.04 ± 1.14 | −9.26 ± 0.36 | −20.20 ± 1.51 | −21.36 ± 1.08 | −44.82 ± 1.54 |
| Ex. 3 | | | −10.14 ± 0.72 | −21.18 ± 1.98 | | |
| Ex. 4 | | | −11.58 ± 0.85 | −23.64 ± 1.70 | −19.98 ± 1.63 | −43.88 ± 3.71 |
| Ex. 5 | | | −12.30 ± 2.20 | −25.40 ± 4.56 | | |
| Ex. 6 | | | −11.72 ± 1.78 | −24.02 ± 3.31 | | |
| Ex. 7 | −5.26 ± 0.49 | −12.22 ± 1.19 | −8.38 ± 0.50 | −19.65 ± 1.27 | −16.26 ± 2.23 | |
| Ex. 10 | −5.4 ± 0.49 | −12.70 ± 1.17 | −10.98 ± 0.76 | −24.95 ± 1.99 | −17.08 ± 1.43 | −39.51 ± 3.84 |
| Ex. 11 | −7.22 ± 0.38 | −16.58 ± 0.88 | −11.82 ± 1.72 | −26.83 ± 4.04 | −16.48 ± 1.98 | −37.35 ± 3.91 |
| Ex. 12 | −8.40 ± 0.77 | −19.33 ± 1.66 | −10.34 ± 0.69 | −23.37 ± 1.40 | −17.44 ± 1.37 | −46.60 ± 3.78 |
| Ex. 13 | −4.92 ± 0.86 | −10.14 ± 1.87 | −11.02 ± 0.77 | −23.80 ± 1.25 | −21.12 ± 2.09 | |
| Ex. 14 | −6.12 ± 0.80 | −13.38 ± 1.80 | −14.76 ± 1.06 | −32.32 ± 2.49 | −20.04 ± 2.40 | −45.26 ± 4.79 |
| Ex. 16 | −7.44 ± 0.74 | −16.78 ± 1.88 | −12.24 ± 1.66 | −28.08 ± 4.23 | −16.70 ± 1.67 | −37.42 ± 3.58 |
| Ex. 18 | | | −13.16 ± 0.82 | −28.48 ± 2.05 | −19.54 ± 2.37 | −43.02 ± 4.59 |
| Ex. 20 | −4.18 ± 0.50 | −8.98 ± 1.26 | −10.76 ± 1.57 | −24.42 ± 3.74 | −23.00 ± 0.59 | −52.14 ± 1.74 |
| Sema | | −2.62 ± 0.49 | | −10.31 ± 1.25 | | −15.49 ± 2.44 |

NOTE:
"Δ from vehicle" refers to difference between body weight at day 15 between test and vehicle groups.
"% change" refers to percent decrease in body weight between days 1 and 15 in test groups.
"Sema" means semaglutide.
Percent decrease in body weight for animals receiving vehicle is recorded, and is less than about 1% in each study.
The Δ from vehicle and % change data are statistically significantly different (p <0.05) than control for all Examples at all doses tested.

As seen in Table 7 above, the exemplary analogs show dose-dependent reductions in body weight.

Data for metabolic parameters at the 3 nmol/kg dose are provided below in Table 8.

TABLE 8

Effect of Treatment with Exemplary Analogs at 3 nmol/kg on Blood Glucose, Insulin, Cholesterol, Alanine Aminotransferase (ALT) and Liver Triglycerides After Fifteen Days of Treatment.

| Treatment | Metabolic Parameters (Mean ± SEM) | | | | |
|---|---|---|---|---|---|
| | Glucose (mg/dL) | Plasma Insulin (pg/mL) | Cholesterol (mg/dL) | ALT (IU/L) | Liver Triglycerides (mg/g tissue) |
| Vehicle | 149.7 ± 3.09 | 8549 ± 1265 | 234.6 ± 3.42 | 141.8 ± 11.5 | 290.4 ± 13.3 |
| Semaglutide | 137.8 ± 7.34 | 4196 ± 1014* | 218.0 ± 9.23 | 99.8 ± 14.84 | 226.4 ± 23.8 |
| Example 1 | 107.4 ± 4.38* | 3439 ± 936.4* | 191.2 ± 7.55* | 118.0 ± 20.73 | 150.6 ± 37.0* |
| Example 7 | 109.3 ± 5.78* | 2656 ± 949* | 169.2 ± 11.79* | 51.0 ± 7.78* | 97.9 ± 18.2* |
| Example 10 | 109.6 ± 4.81* | 571.4 ± 158.4* | 181.0 ± 6.20* | 77.2 ± 9.35* | 126.8 ± 17.0* |
| Example 11 | 114.7 ± 3.051* | 1569 ± 318.3* | 178.2 ± 7.95* | 56.2 ± 4.51* | 93.8 ± 21.8* |
| Example 12 | 114.9 ± 2.12* | 1691 ± 231.3* | 169.0 ± 8.15* | 58.6 ± 6.03* | 98.2 ± 13.2* |
| Example 13 | 119.7 ± 4.19* | 2903 ± 737.4* | 192.2 ± 11.44* | 54.4 ± 6.82* | 94.5 ± 22.0* |
| Example 14 | 111.5 ± 1.77* | 1971 ± 499.8* | 164.8 ± 5.85* | 31.4 ± 2.79* | 63.1 ± 7.3* |
| Example 16 | 110.1 ± 3.61* | 3227 ± 1070* | 173.8 ± 9.32* | 20.6 ± 4.43* | 40.2 ± 13.2* |
| Example 18 | 102.9 ± 5.37* | 1958 ± 460.5* | 190.0 ± 13.71* | 66.0 ± 10.21* | 109.5 ± 22.9* |

NOTE: *p < 0.05 compared to Vehicle group; one-way ANOVA, Dunnett's.

In addition to substantial weight loss, and as seen in Table 8, the exemplary analogs reduce blood glucose, plasma insulin (as a sign of increasing insulin sensitivity) and plasma cholesterol, as well as improve liver health demonstrated by decrease of plasma ALT and liver triglycerides.

```
Human glucagon
                                                    SEQ ID NO: 1
HSQGTFTSDYSKYLDSRRAQDFVQWLMNT Human GLP-1 (7-36) amide
                                                    SEQ ID NO: 2
HAEGTFTSDVSSYLEGQAAKEFIAWLVKGR-NH2

Human OXM
                                                    SEQ ID NO: 3
HSQGTFTSDYSKYLDSRRAQDFVQWLMNTKRNRNNIA Human GIP
                                                    SEQ ID NO: 4
YAEGTFISDYSIAMDKIHQQDFVNWLLAQKGKKNDWKHNITQ Incretin analog
                                                    SEQ ID NO: 5
YX₂QGTFTSDYSIX₁₃LDKX₁₇AX₁₉X₂₀AFIEYLLX₂₈X₂₉GPSSX₃₄APPPS
where:

X₂ is Aib,

X₁₃ is L or αMeL,

X₁₇ is any amino acid with a functional group available for conjugation,
and the functional group is conjugated to a C₁₆-C₂₂ fatty acid, X₁₉ is Q or A, X₂₀ is Aib, αMeK, Q or H, X₂₈ is E or A, X₂₉ is G or Aib, and X₃₄ is G or Aib
```

-continued

Incretin analog
SEQ ID NO: 6
Y-Aib-QGTFTSDYSI-αMeL-LDKK((2-[2-(2-amino-ethoxy)-ethoxy]-acetyl)-(γGlu)-

CO—(CH$_2$)$_{18}$—CO$_2$H)AQHAFIEYLLA-Aib-GPSSGAPPPS-NH$_2$

Incretin analog
SEQ ID NO: 7
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AQ-αMeK-AFIEYLLA-Aib-GPSSGAPPPS-NH$_2$

Incretin analog
SEQ ID NO: 8
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AQ-αMeK-AFIEYLLEGGPSSGAPPPS-NH$_2$

Incretin analog
SEQ ID NO: 9
Y-Aib-QGTFTSDYSILLDKK((2-[2-(2-amino-ethoxy)-ethoxy]-acetyl)-(γGlu)-

CO—(CH$_2$)$_{18}$—CO$_2$H)AQ-Aib-AFIEYLLA-Aib-GPSSGAPPPS-NH$_2$

Incretin analog
SEQ ID NO: 10
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AAQAFIEYLLE-Aib-GPSSGAPPPS-NH$_2$

Incretin analog
SEQ ID NO: 11
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AAQAFIEYLLEGGPSSGAPPPS-NH$_2$

Incretin analog
SEQ ID NO: 12
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AQHAFIEYLLEGGPSSGAPPPS-NH$_2$

Incretin analog
SEQ ID NO: 13
Y-Aib-QGTFTSDYSILLDKK((2-[2-(2-amino-ethoxy)-ethoxy]-acetyl)$_2$-(γGlu)-

CO—(CH$_2$)$_{18}$—CO$_2$H)AQ-αMeK-AFIEYLLEGGPSSGAPPPS-NH$_2$

Incretin analog
SEQ ID NO: 14
Y-Aib-QGTFTSDYSI-αMeL-LDKK((γGlu)$_2$-CO—(CH$_2$)$_{18}$—CO$_2$H)AQHAFIEYLLEGGPSSGAPPPS-NH$_2$ Incretin analog
SEQ ID NO: 15
Y-Aib-QGTFTSDYSI-αMeL-LDKK((2-[2-(2-amino-ethoxy)-ethoxy]-acetyl)-(γGlu)-

CO—(CH$_2$)$_{18}$—CO$_2$H)AQHAFIEYLLEGGPSSGAPPPS-NH$_2$

Incretin analog
SEQ ID NO: 16
Y-Aib-QGTFTSDYSI-αMeL-LDKK((2-[2-(2-amino-ethoxy)-ethoxy]-acetyl)$_2$-(γGlu)-

CO—(CH$_2$)$_{18}$—CO$_2$H)AQ-Aib-AFIEYLLEGGPSSGAPPPS-NH$_2$

Incretin analog
SEQ ID NO: 17
Y-Aib-QGTFTSDYSI-αMeL-LDKK((2-[2-(2-amino-ethoxy)-ethoxy]-acetyl)-(γGlu)-

CO—(CH$_2$)$_{18}$—CO$_2$H)AQ-Aib-AFIEYLLEGGPSSGAPPPS-NH$_2$

Incretin analog
SEQ ID NO: 18
Y-Aib-QGTFTSDYSI-αMeL-LDKK((2-[2-(2-amino-ethoxy)-ethoxy]-acetyl)-(γGlu)-

CO—(CH$_2$)$_{18}$—CO$_2$H)AQ-Aib-AFIEYLLE-Aib-GPSSGAPPPS-NH$_2$

Incretin analog
SEQ ID NO: 19
Y-Aib-QGTFTSDYSI-αMeL-LDKK((2-[2-(2-amino-ethoxy)-ethoxy]-acetyl)-(γGlu)-

CO—(CH$_2$)$_{18}$—CO$_2$H)AQ-Aib-AFIEYLLE-Aib-GPSS-Aib-APPPS-NH$_2$

Incretin analog

SEQ ID NO: 20

Y-Aib-QGTFTSDYSILLDKK((2-[2-(2-amino-ethoxy)-ethoxy]-acetyl)$_2$-(γGlu)-CO—(CH$_2$)$_{18}$—CO$_2$H)AQ-Aib-AFIEYLLA-Aib-GPSSGAPPPS-NH$_2$ Incretin analog

SEQ ID NO: 21

Y-Aib-QGTFTSDYSILLDKK((2-[2-(2-amino-ethoxy)-ethoxy]-acetyl)$_2$-(γGlu)-CO—(CH$_2$)$_{18}$—CO$_2$H)AQ-Aib-AFIEYLLEGGPSSGAPPPS-NH$_2$ Incretin analog

SEQ ID NO: 22

Y-Aib-QGTFTSDYSILLDKK((2-[2-(2-amino-ethoxy)-ethoxy]-acetyl)$_2$-(γGlu)-CO—(CH$_2$)$_{18}$—CO$_2$H)AQ-Aib-AFIEYLLE-Aib-GPSSGAPPPS-NH$_2$ Incretin analog

SEQ ID NO: 23

Y-Aib-QGTFTSDYSILLDKK((2-[2-(2-amino-ethoxy)-ethoxy]-acetyl)-(γGlu)-CO—(CH$_2$)$_{18}$—CO$_2$H)AQ-Aib-AFIEYLLEGGPSSGAPPPS-NH$_2$ Incretin analog

SEQ ID NO: 24

Y-Aib-QGTFTSDYSILLDKK((2-[2-(2-amino-ethoxy)-ethoxy]-acetyl)-(γGlu)$_2$-CO—(CH$_2$)$_{18}$—CO$_2$H)AQ-Aib-AFIEYLLE-Aib-GPSSGAPPPS-NH$_2$ Incretin analog

SEQ ID NO: 25

Y-Aib-QGTFTSDYSILLDKK((2-[2-(2-amino-ethoxy)-ethoxy]-acetyl)-(γGlu)-CO—(CH$_2$)$_{18}$—CO$_2$H)AQ-Aib-AFIEYLLE-Aib-GPSSGAPPPS-NH$_2$ Artificial sequence

SEQ ID NO: 26

GPSSGAPPPS

Artificial sequence

SEQ ID NO: 27

GPSS-Aib-APPPS

---

SEQUENCE LISTING

<160> NUMBER OF SEQ ID NOS: 27

<210> SEQ ID NO 1
<211> LENGTH: 29
<212> TYPE: PRT
<213> ORGANISM: Homo sapiens

<400> SEQUENCE: 1

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 2
<211> LENGTH: 30
<212> TYPE: PRT
<213> ORGANISM: Homo sapiens

<400> SEQUENCE: 2

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

```
<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 4
<211> LENGTH: 42
<212> TYPE: PRT
<213> ORGANISM: Homo sapiens

<400> SEQUENCE: 4

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 5
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is Leu or alpha-methyl-Leu
<220> FEATURE:
<221> NAME/KEY: MISC_FEATURE
<222> LOCATION: (17)..(17)
<223> OTHER INFORMATION: Xaa at position 17 is any amino acid with a
      functional group available for conjugation wherein the functional
      group is conjugated to a C16-C22 fatty acid
<220> FEATURE:
<221> NAME/KEY: MISC_FEATURE
<222> LOCATION: (19)..(19)
<223> OTHER INFORMATION: Xaa at position 19 is Gln or Ala
<220> FEATURE:
<221> NAME/KEY: MISC_FEATURE
<222> LOCATION: (20)..(20)
<223> OTHER INFORMATION: Xaa at position 20 is Aib, alpha-methyl-Lys,
      Gln, or His
<220> FEATURE:
<221> NAME/KEY: MISC_FEATURE
<222> LOCATION: (28)..(28)
<223> OTHER INFORMATION: Xaa at position 28 is Glu or Ala
<220> FEATURE:
<221> NAME/KEY: MISC_FEATURE
<222> LOCATION: (29)..(29)
<223> OTHER INFORMATION: Xaa at position 29 is Gly or Aib
<220> FEATURE:
<221> NAME/KEY: MISC_FEATURE
<222> LOCATION: (34)..(34)
<223> OTHER INFORMATION: Xaa at position 34 is Gly or Aib

<400> SEQUENCE: 5

Tyr Xaa Gln Gly Thr Phe Thr Ser Asp Tyr Ser Ile Xaa Leu Asp Lys
```

```
                 1               5                  10                  15
Xaa Ala Xaa Xaa Ala Phe Ile Glu Tyr Leu Leu Xaa Xaa Gly Pro Ser
                20                  25                  30
Ser Xaa Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (17)..(17)
<223> OTHER INFORMATION: Lys at position 17 is modified with
      (2-[2-(2-Amino-ethoxy)-ethoxy]-acetyl)-(gamma-Glu)-CO-(CH2)18-
      HCO2H
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 6

Tyr Xaa Gln Gly Thr Phe Thr Ser Asp Tyr Ser Ile Xaa Leu Asp Lys
1               5                  10                  15
Lys Ala Gln His Ala Phe Ile Glu Tyr Leu Leu Ala Xaa Gly Pro Ser
                20                  25                  30
Ser Gly Ala Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H)
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
```

```
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 7

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Ala Xaa Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is 2-aminoisobutyric acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H)
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MOD_RES
<222> LOCATION: (39)..(39)
<223> OTHER INFORMATION: Ser at position 39 is optionally amidated

<400> SEQUENCE: 8

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is 2-aminoisobutyric acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
```

```
              CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 9

Tyr Xaa Gln Gly Thr Phe Thr Ser Asp Tyr Ser Ile Leu Leu Asp Lys
1               5                   10                  15

Lys Ala Gln Xaa Ala Phe Ile Glu Tyr Leu Leu Ala Xaa Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 10

Tyr Xaa Gln Gly Thr Phe Thr Ser Asp Tyr Ser Ile Xaa Leu Asp Lys
1               5                   10                  15

Lys Ala Ala Gln Ala Phe Ile Glu Tyr Leu Leu Glu Xaa Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is optionally amidated

<400> SEQUENCE: 11

Tyr Xaa Gln Gly Thr Phe Thr Ser Asp Tyr Ser Ile Xaa Leu Asp Lys
1               5                   10                  15

Lys Ala Ala Gln Ala Phe Ile Glu Tyr Leu Leu Glu Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is optionally amidated

<400> SEQUENCE: 12

Tyr Xaa Gln Gly Thr Phe Thr Ser Asp Tyr Ser Ile Xaa Leu Asp Lys
1               5                   10                  15

Lys Ala Gln His Ala Phe Ile Glu Tyr Leu Leu Glu Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MOD_RES
<222> LOCATION: (39)..(39)
<223> OTHER INFORMATION: Ser at position 39 is optionally amidated

<400> SEQUENCE: 13

Tyr Xaa Gln Gly Thr Phe Thr Ser Asp Tyr Ser Ile Leu Leu Asp Lys
 1               5                  10                  15

Lys Ala Gln Xaa Ala Phe Ile Glu Tyr Leu Leu Glu Gly Gly Pro Ser
             20                  25                  30

Ser Gly Ala Pro Pro Pro Ser
             35

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (gamma-Glu)2-CO-(CH2)18-CO2H
<220> FEATURE:
<221> NAME/KEY: MOD_RES
<222> LOCATION: (39)..(39)
<223> OTHER INFORMATION: Ser at position 39 is optionally amidated

<400> SEQUENCE: 14

Tyr Xaa Gln Gly Thr Phe Thr Ser Asp Tyr Ser Ile Xaa Leu Asp Lys
 1               5                  10                  15

Lys Ala Gln His Ala Phe Ile Glu Tyr Leu Leu Glu Gly Gly Pro Ser
             20                  25                  30

Ser Gly Ala Pro Pro Pro Ser
             35

<210> SEQ ID NO 15
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
```

```
                               acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is optionally amidated

<400> SEQUENCE: 15

Tyr Xaa Gln Gly Thr Phe Thr Ser Asp Tyr Ser Ile Xaa Leu Asp Lys
1               5                   10                  15

Lys Ala Gln His Ala Phe Ile Glu Tyr Leu Leu Glu Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic Consruct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 16

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic Construct
```

```
-continued

<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 2 is alpha-methyl-leucine
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 17

Tyr Xaa Gln Gly Thr Phe Thr Ser Asp Tyr Ser Ile Xaa Leu Asp Lys
 1               5                  10                  15

Lys Ala Gln Xaa Ala Phe Ile Glu Tyr Leu Leu Glu Gly Gly Pro Ser
                20                  25                  30

Ser Gly Ala Pro Pro Pro Ser
            35

<210> SEQ ID NO 18
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 18

Tyr Xaa Gln Gly Thr Phe Thr Ser Asp Tyr Ser Ile Xaa Leu Asp Lys
 1               5                  10                  15
```

-continued

```
Lys Ala Gln Xaa Ala Phe Ile Glu Tyr Leu Leu Glu Xaa Gly Pro Ser
            20                  25                  30

Ser Gly Ala Pro Pro Pro Ser
            35
```

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamm-Glu)-CO-(CH2)18-CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MISC_FEATURE
<222> LOCATION: (34)..(34)
<223> OTHER INFORMATION: Xaa at position 34 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 19

```
Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Xaa Gly Pro Ser
            20                  25                  30

Ser Xaa Ala Pro Pro Pro Ser
            35
```

<210> SEQ ID NO 20
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H

```
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 20

Tyr Xaa Gln Gly Thr Phe Thr Ser Asp Tyr Ser Ile Leu Leu Asp Lys
1               5                  10                  15

Lys Ala Gln Xaa Ala Phe Ile Glu Tyr Leu Leu Ala Xaa Gly Pro Ser
                20                  25                  30

Ser Gly Ala Pro Pro Pro Ser
                35

<210> SEQ ID NO 21
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 21

Tyr Xaa Gln Gly Thr Phe Thr Ser Asp Tyr Ser Ile Leu Leu Asp Lys
1               5                  10                  15

Lys Ala Gln Xaa Ala Phe Ile Glu Tyr Leu Leu Glu Gly Gly Pro Ser
                20                  25                  30

Ser Gly Ala Pro Pro Pro Ser
                35

<210> SEQ ID NO 22
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
```

```
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 22

Tyr Xaa Gln Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Xaa Gly Pro Ser
            20                  25                  30

Ser Gly Ala Pro Pro Pro Ser
            35

<210> SEQ ID NO 23
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 23

Tyr Xaa Gln Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
            35

<210> SEQ ID NO 24
<211> LENGTH: 39
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)2-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 24

Tyr Xaa Gln Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Xaa Gly Pro Ser
            20                  25                  30

Ser Gly Ala Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-amino-isobutyric
      acid
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-amino-isobutyric
      acid
<220> FEATURE:
<221> NAME/KEY: MISC_FEATURE
<222> LOCATION: (29)..(29)
<223> OTHER INFORMATION: Xaa at position 29 is alpha-amino-isobutyric
      acid
<220> FEATURE:
<221> NAME/KEY: MOD_RES
<222> LOCATION: (39)..(39)
<223> OTHER INFORMATION: Ser at position 39 is optionally amidated

<400> SEQUENCE: 25

Tyr Xaa Gln Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Xaa Gly Pro Ser
            20                  25                  30
```

```
Ser Gly Ala Pro Pro Ser
            35

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Gly Pro Ser Ser Gly Ala Pro Pro Pro Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa at position 5 is alpha-amino-isobutyric
      acid

<400> SEQUENCE: 27

Gly Pro Ser Ser Xaa Ala Pro Pro Pro Ser
1               5                   10
```

The invention claimed is:

1. An incretin analog comprising:

$YX_2QGTFTSDYSIX_{13}LDKX_{17}AX_{19}X_{20}AFIEYLLX_{28}X_{29}GPSSX_{34}APPPS$, wherein:
 $X_2$ is Aib,
 $X_{13}$ is L or αMeL,
 $X_{17}$ is any amino acid with a functional group available for conjugation selected from the group consisting of K, C, E and D, and the functional group is conjugated to a $C_{16}$-$C_{22}$ fatty acid,
 $X_{19}$ is Q or A,
 $X_{20}$ is Aib, αMeK, Q or H,
 $X_{28}$ is E or A,
 $X_{29}$ is G or Aib,
 $X_{34}$ is G or Aib,
 (SEQ ID NO:5), and
wherein the C-terminal amino acid is optionally amidated; or a pharmaceutically acceptable salt thereof.

2. The incretin analog of claim 1, wherein the amino acid with the functional group available for conjugation at position $X_{17}$ is K.

3. The incretin analog of claim 1, wherein the amino acid with the functional group available for conjugation at position $X_{17}$ and the $C_{16}$-$C_{22}$ fatty acid are conjugated by a linker between the amino acid and the fatty acid.

4. The incretin analog of claim 3, wherein the linker comprises one to four amino acids.

5. The incretin analog of claim 4, wherein the amino acids are Glu or γGlu.

6. The incretin analog of claim 3, wherein the linker further comprises a structure of:
H—{NH—$CH_2$—$CH_2$[O—$CH_2$—$CH_2$]$_m$—O—$(CH_2)_p$—CO}$_n$—OH, wherein m is any integer from 1 to 12, n is any integer from 1 to 12, and p is 1 or 2.

7. The incretin analog of claim 3, wherein the linker further comprises one to four (2-[2-(2-amino-ethoxy)-ethoxy]-acetyl) moieties.

8. The incretin analog of claim 1, wherein $X_{17}$ is a K chemically modified through conjugation to an epsilon-amino group of a K side-chain with the following structure:
 (2-[2-(2-amino-ethoxy)-ethoxy]-acetyl)$_a$-(γGlu)$_b$-CO—$(CH_2)_c$—$CO_2H$, wherein a is 0, 1 or 2; b is 1 or 2; and c is an integer between 16 to 18.

9. The incretin analog of claim 8, wherein a is 1.

10. The incretin analog of claim 8, wherein b is 1.

11. The incretin analog of claim 8, wherein c is 18.

12. The incretin analog of claim 1, wherein $X_{13}$ is αMeL.

13. The incretin analog of claim 1, wherein $X_{20}$ is Aib.

14. The incretin analog of claim 1, wherein $X_{28}$ is E.

15. The incretin analog of claim 1, wherein $X_{29}$ is G.

16. The incretin analog of claim 1, wherein $X_{34}$ is G.

17. The incretin analog of claim 1, wherein $X_{19}$ is Q.

18. The incretin analog of claim 8, wherein a is 1, b is 1, c is 18, $X_{13}$ is αMeL, $X_{19}$ is Q, $X_{20}$ is Aib, $X_{28}$ is E, $X_{29}$ is G and $X_{34}$ is G.

19. An incretin analog having a formula selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:16, SEQ ID NO:17, SEQ ID NO:18, SEQ ID NO:19, SEQ ID NO:21 SEQ ID NO:23 and SEQ ID NO:25, or a pharmaceutically acceptable salt thereof.

20. A method of treating a disease selected from the group consisting of diabetes mellitus, obesity, fatty liver disease, non-alcoholic steatohepatitis, dyslipidemia and metabolic syndrome, the method comprising a step of:
 administering to an individual in need thereof an effective amount of an incretin analog of claim 1.

21. The method of claim 20, wherein the disease is obesity or type II diabetes mellitus.

22. A pharmaceutical composition comprising:
an incretin analog of claim 1; and
a pharmaceutically acceptable carrier, diluent or excipient.

23. The method of claim 20, wherein the disease is obesity.

24. The method of claim 20, wherein the disease is type II diabetes mellitus.

25. The incretin analog of claim 19, having a formula of SEQ ID NO: 17, or a pharmaceutically acceptable salt thereof.

26. An incretin analog having a formula

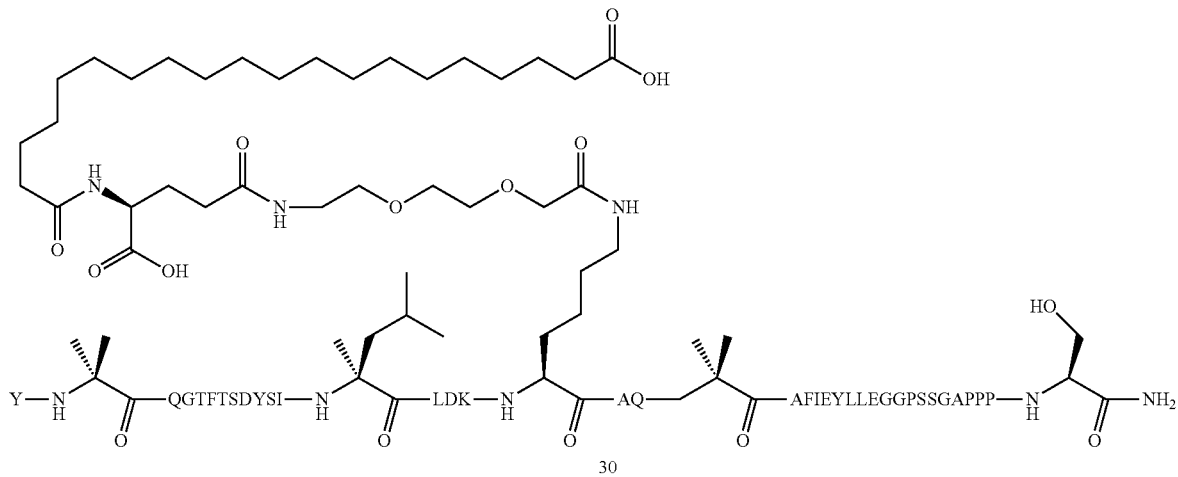

(SEQ ID NO:17) or a pharmaceutically acceptable salt thereof.

* * * * *